(12) United States Patent
Daksis et al.

(10) Patent No.: US 6,403,313 B1
(45) Date of Patent: Jun. 11, 2002

(54) FLUORESCENT INTENSITY ASSAY FOR DUPLEX AND TRIPLEX NUCLEIC ACID HYBRIDIZATION SOLUTION UTILIZING FLUORESCENT INTERCALATORS

(75) Inventors: Jasmine I. Daksis, Richmond Hill; Pierre Picard, Brampton; Glen H. Erikson, Mississauga, all of (CA)

(73) Assignee: Ingeneus Corporation, Bridgetown (BB)

( * ) Notice: Subject to any disclaimer, the term of this patent is extended or adjusted under 35 U.S.C. 154(b) by 0 days.

(21) Appl. No.: 09/468,679

(22) Filed: Dec. 21, 1999

(51) Int. Cl.[7] ............... C12Q 1/68; C12P 19/34; C12M 1/36; C07H 21/04
(52) U.S. Cl. ............... 435/6; 435/91.1; 435/91.2; 435/91.21; 435/287.2; 536/24.3; 536/25.32
(58) Field of Search ............... 435/6, 91.2, 287.2, 435/91.1, 91.21; 536/243, 25.32

(56) References Cited

U.S. PATENT DOCUMENTS

| | | | |
|---|---|---|---|
| 4,220,450 A | | 9/1980 | Maggio |
| 4,876,187 A | | 10/1989 | Duck et al. ............... 435/6 |
| 4,963,477 A | | 10/1990 | Tchen ............... 435/6 |
| 5,011,769 A | | 4/1991 | Duck et al. ............... 435/6 |
| 5,332,659 A | | 7/1994 | Kidwell |
| 5,403,711 A | | 4/1995 | Walder et al. ............... 435/6 |
| 5,538,848 A | | 7/1996 | Livak et al. |
| 5,539,082 A | | 7/1996 | Nielsen et al. ............... 500/300 |
| 5,558,998 A | * | 9/1996 | Hammond et al. ............... 435/6 |
| 5,660,988 A | | 8/1997 | Duck et al. ............... 435/6 |
| 5,705,346 A | * | 1/1998 | Okamoto et al. ............... 435/6 |
| 5,707,801 A | | 1/1998 | Bresser et al. ............... 435/6 |
| 5,731,146 A | | 3/1998 | Duck et al. ............... 435/6 |
| 5,800,984 A | * | 9/1998 | Vary ............... 435/6 |
| 5,800,992 A | * | 9/1998 | Fodor et al. ............... 435/6 |
| 5,814,447 A | * | 9/1998 | Ishiguro et al. ............... 435/6 |
| 5,814,516 A | | 9/1998 | Vo-Dinh ............... 435/287.2 |
| 5,824,477 A | | 10/1998 | Stanley ............... 435/6 |
| 5,824,557 A | | 10/1998 | Burke et al. |
| 5,846,729 A | * | 12/1998 | Wu et al. ............... 435/6 |
| 5,861,124 A | | 1/1999 | Hosoi et al. ............... 422/82.02 |

(List continued on next page.)

FOREIGN PATENT DOCUMENTS

JP           5237000          9/1993

OTHER PUBLICATIONS

Baran et al., *Nucleic Acids Research* 25:297–303 (1997).
Bohmann et al., *Science*, 238:1386–1392 (Dec. 1987).
Chan et al., *J. Mol. Med.* 75 Issue 4:267–282 (1997).
Dalrymple et al., *Nucleic Acids Research*, vol. 13, No. 21, pp. 7865–7879 (1985).
Durland et al., *Biochemistry*, 30:9246–9255 (1991).
Floris et al., 260 Eur. J. Biochem. 801–809 (1999).
Hill et al., *Methods in Enzymology*, 278:390–416 (1997).

(List continued on next page.)

*Primary Examiner*—W. Gary Jones
*Assistant Examiner*—B J Forman
(74) *Attorney, Agent, or Firm*—Caesar, Rivise, Bernstein, Cohen & Pokotilow, Ltd.

(57) ABSTRACT

The invention provides a homogeneous assay for nucleic acid hybridization. The fluorescent intensity of a hybridization medium containing a probe, a target and an intercalating agent is a function of the hybridization efficiency of the probe with respect to the target. The assay can detect specific hybridization between single-stranded probes and non-denatured double-stranded targets to form triplexes, thus obviating the need to denature the targets. The assay can also detect duplex hybridization complexes. The assay can be used to identify accessible regions in folded nucleotide sequences, to determine the number of mismatched pairs in a hybridization complex, and to map genomes.

31 Claims, 13 Drawing Sheets

U.S. PATENT DOCUMENTS

| | | | |
|---|---|---|---|
| 5,874,555 A | 2/1999 | Dervan et al. | 536/23.1 |
| 5,888,739 A | 3/1999 | Pitner et al. | 435/6 |
| 5,912,332 A | 6/1999 | Agrawal et al. | 536/23.1 |
| 5,948,897 A | 9/1999 | Sen et al. | 536/22.1 |
| 6,013,442 A * | 1/2000 | Kolesar et al. | 435/6 |
| 6,017,709 A | 2/2000 | Hardin et al. | 435/6 |
| 6,027,880 A | 2/2000 | Cronin et al. | 435/6 |
| 6,046,004 A * | 4/2000 | Wu et al. | 435/6 |
| 6,048,690 A | 4/2000 | Heller et al. | 435/6 |
| 6,060,242 A | 5/2000 | Nie et al. | 435/6 |
| 6,107,078 A | 8/2000 | Keese et al. | 435/252.3 |
| 6,117,657 A | 9/2000 | Usman et al. | 435/91.31 |
| 6,251,591 B1 | 6/2001 | Wu et al. | 435/6 |
| 6,255,050 B1 | 7/2001 | Nie et al. | 435/6 |
| 6,265,170 B1 | 7/2001 | Picard et al. | 435/6 |
| 6,312,925 B1 * | 11/2001 | Meyer, Jr. et al. | 435/91.1 |

OTHER PUBLICATIONS

Johansen and Jacobsen, *J Biomol Struct Dyn*, 16(2):205–22 (1998 Oct) (Abstract).

Kadonaga et al., *Cell*, 51:1079–1090 (Dec. 24, 1987).

Kukreti et al. 25 *Nucleic Acids Research* 4264–4270 (1997).

Marsh et al., *Nucleic Acids Research*, 23:696–700 (1995).

Marsh et al., *Biochemistry* 33:10718–10724 (1994).

Mazumder et al., *Biochemistry* 35:13762–13771 (1996).

Sen et al., *Nature* 334:364–366 ( Jul. 28, 1988).

Sen et al., *Biochemistry* 31:65–70 (1992).

Sturm et al., *Genes & Development*, 2:1582–1599 (1988).

Watson, James, "A Personal Account of the Discovery of the Structure of DNA," (1968).

Williamson et al., *Cell* 59:871–880 (Dec. 1, 1989).

Wilson et al., *Cell*, 74:115–125 (Jul. 16, 1993).

Zhurkin et al., *J. Mol. Biol.*, vol. 239, 181–200 (1994).

Egholm et al., "PNA hybridizes to complementary oligonucleotides obeying the Waston–Crick hydrogen–bonding rules," Nature, vol. 365, pp. 566–568, Oct. 1993.

Carlsson et al., "Screening for genetic mutations," Nature, vol. 380, p. 207, Mar. 21, 1996.

Tomac et al., "Ionic Effects on the Stability and Conformation of Peptide Nucleic Acid Complexes," J. Am. Chem. Soc., vol. 118, pp. 5544–5552, 1996.

* cited by examiner

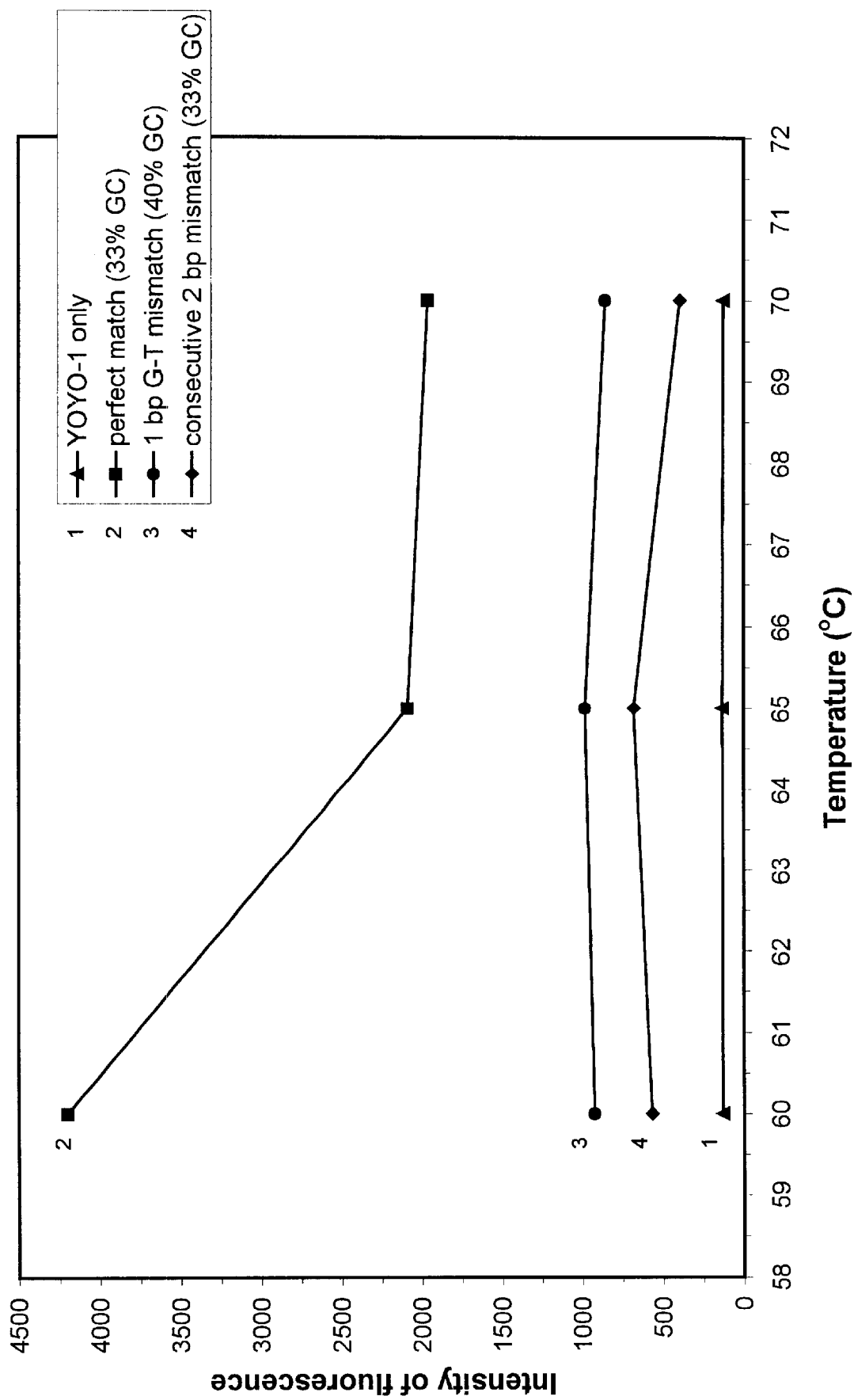

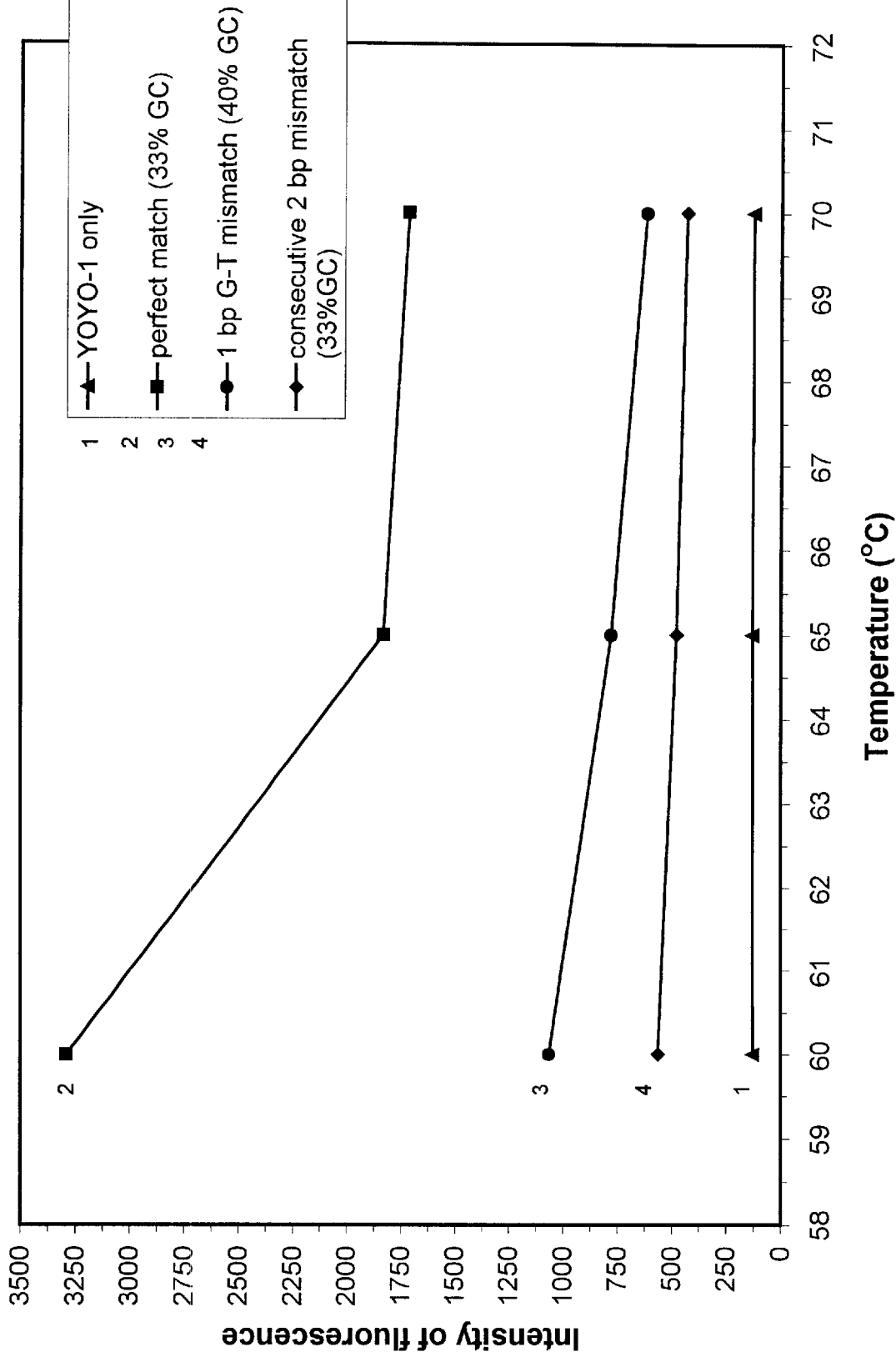
FIG. 1B. 15-mer parallel PNA to 50-mer DNA hybridization with YOYO-1

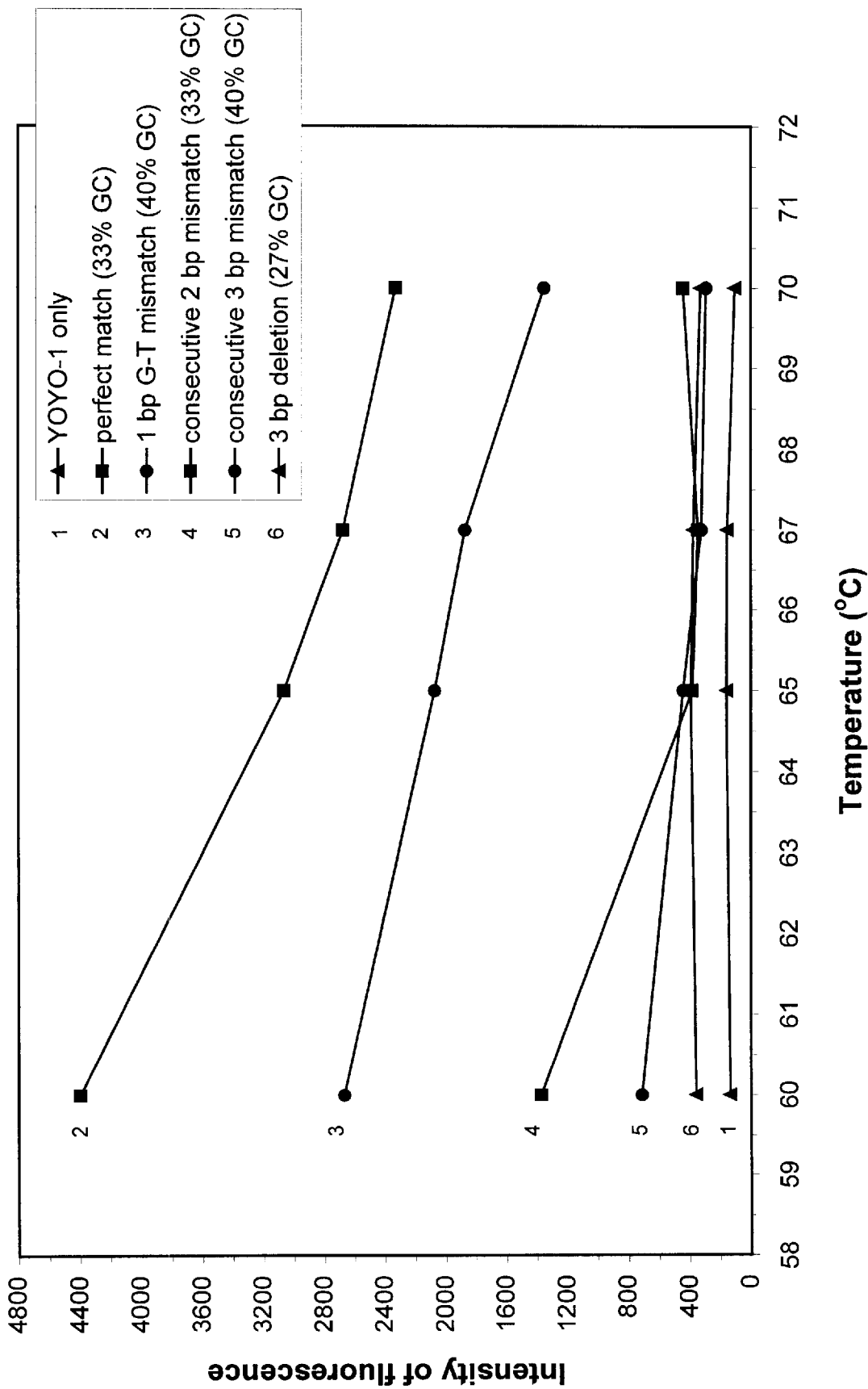
FIG. 2. 15-mer parallel PNA to 50-mer DNA hybridization with YOYO-1

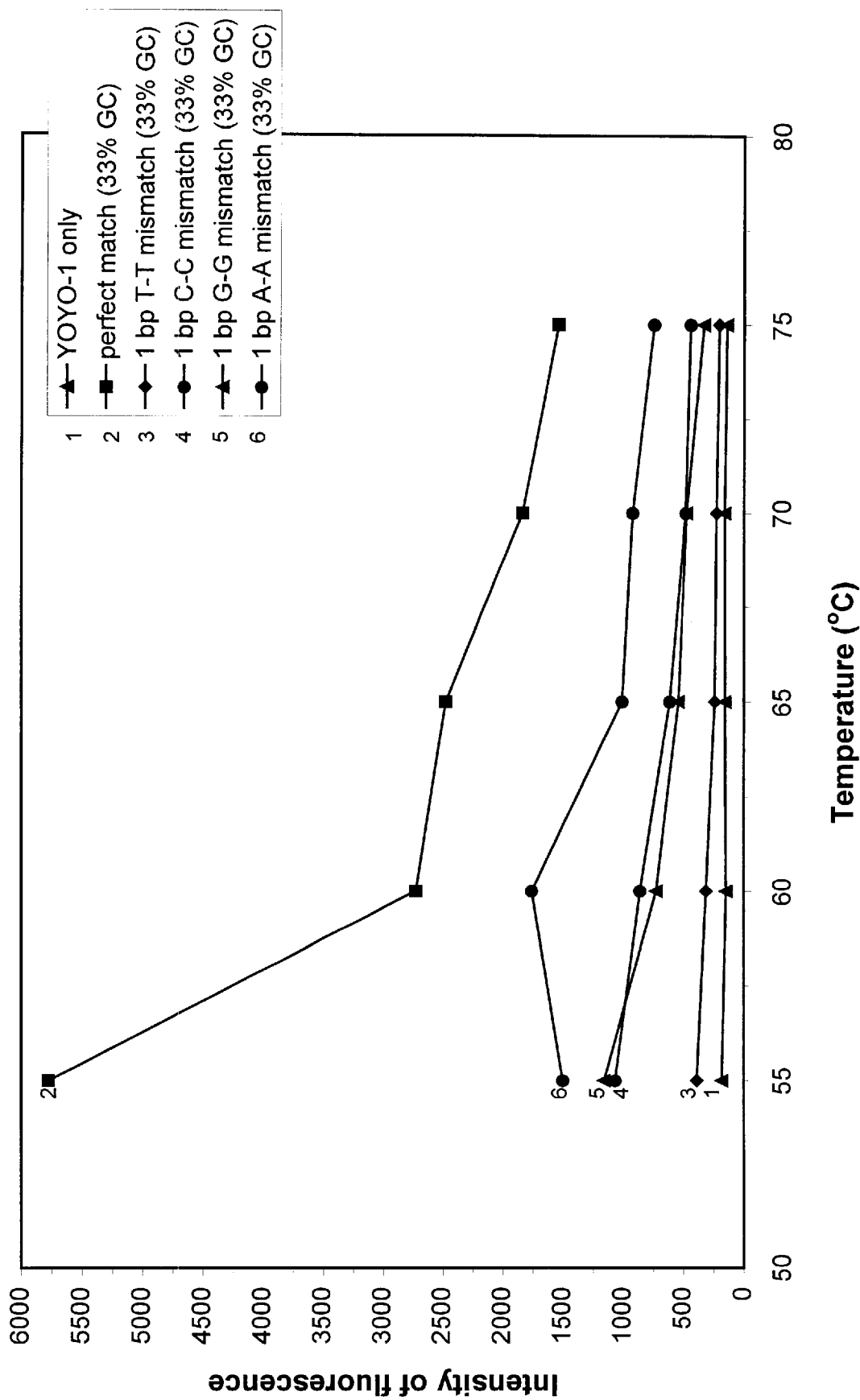

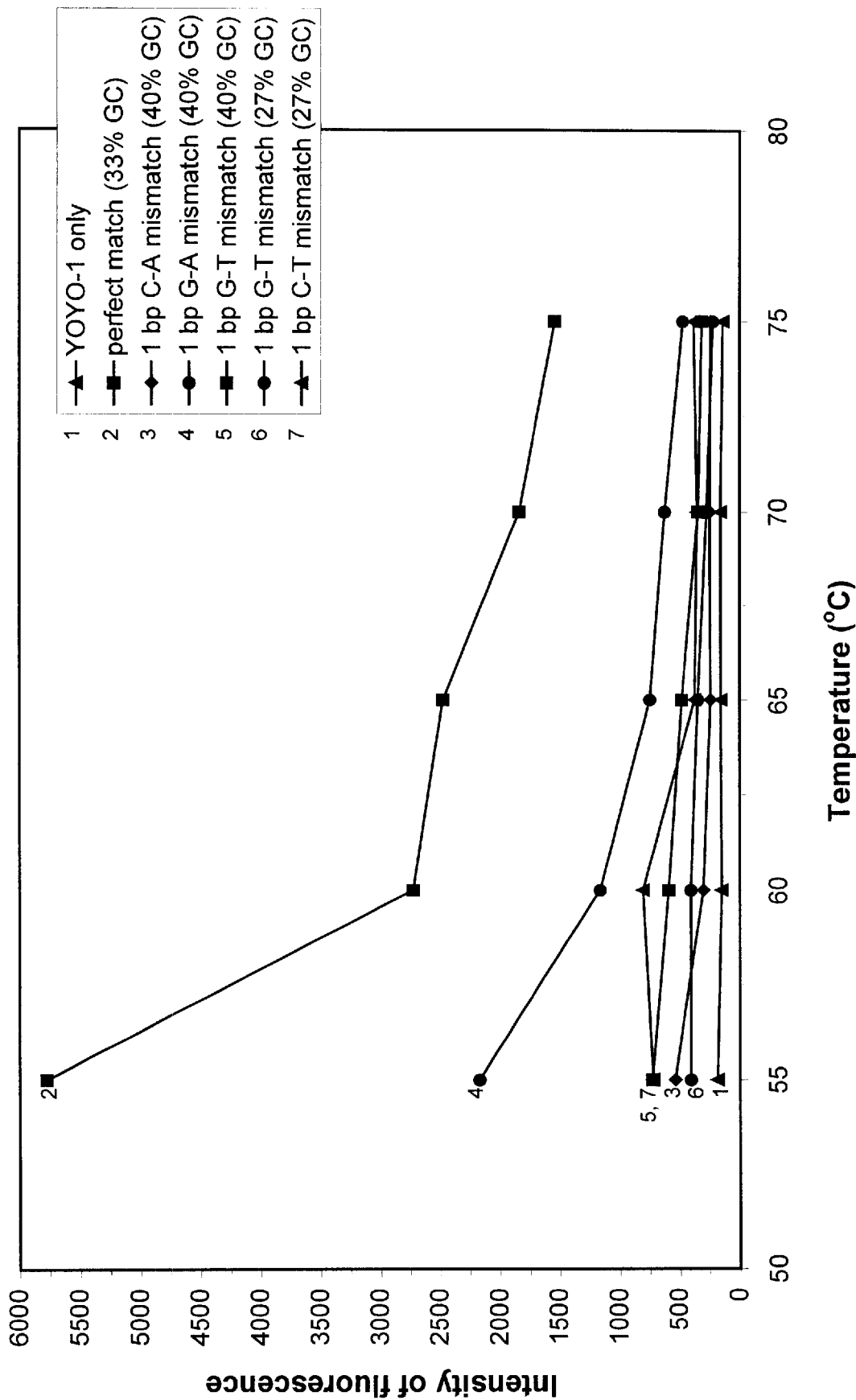

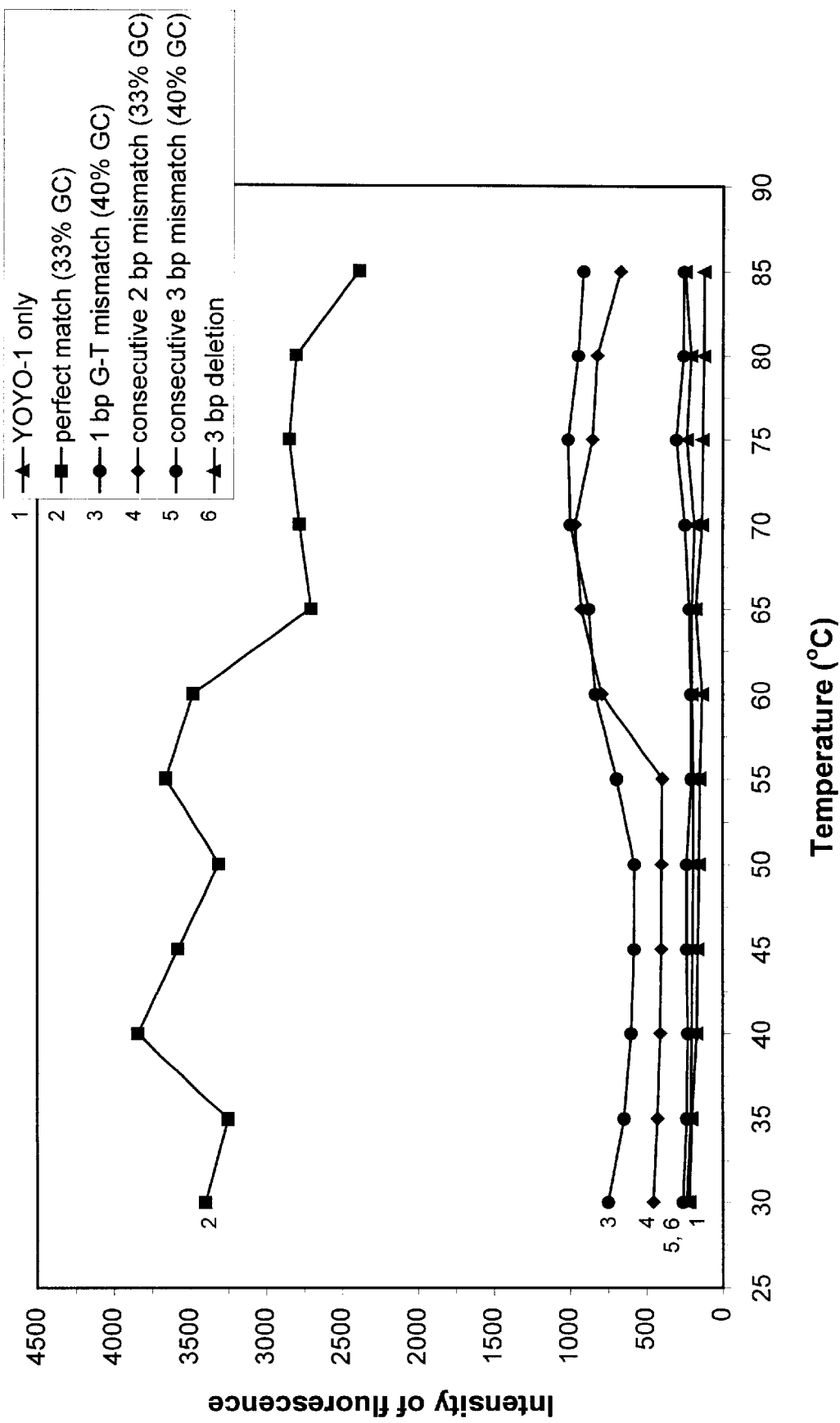
FIG. 4. 15-mer parallel PNA to 50-mer dsDNA hybridization with YOYO-1 without prior denaturation

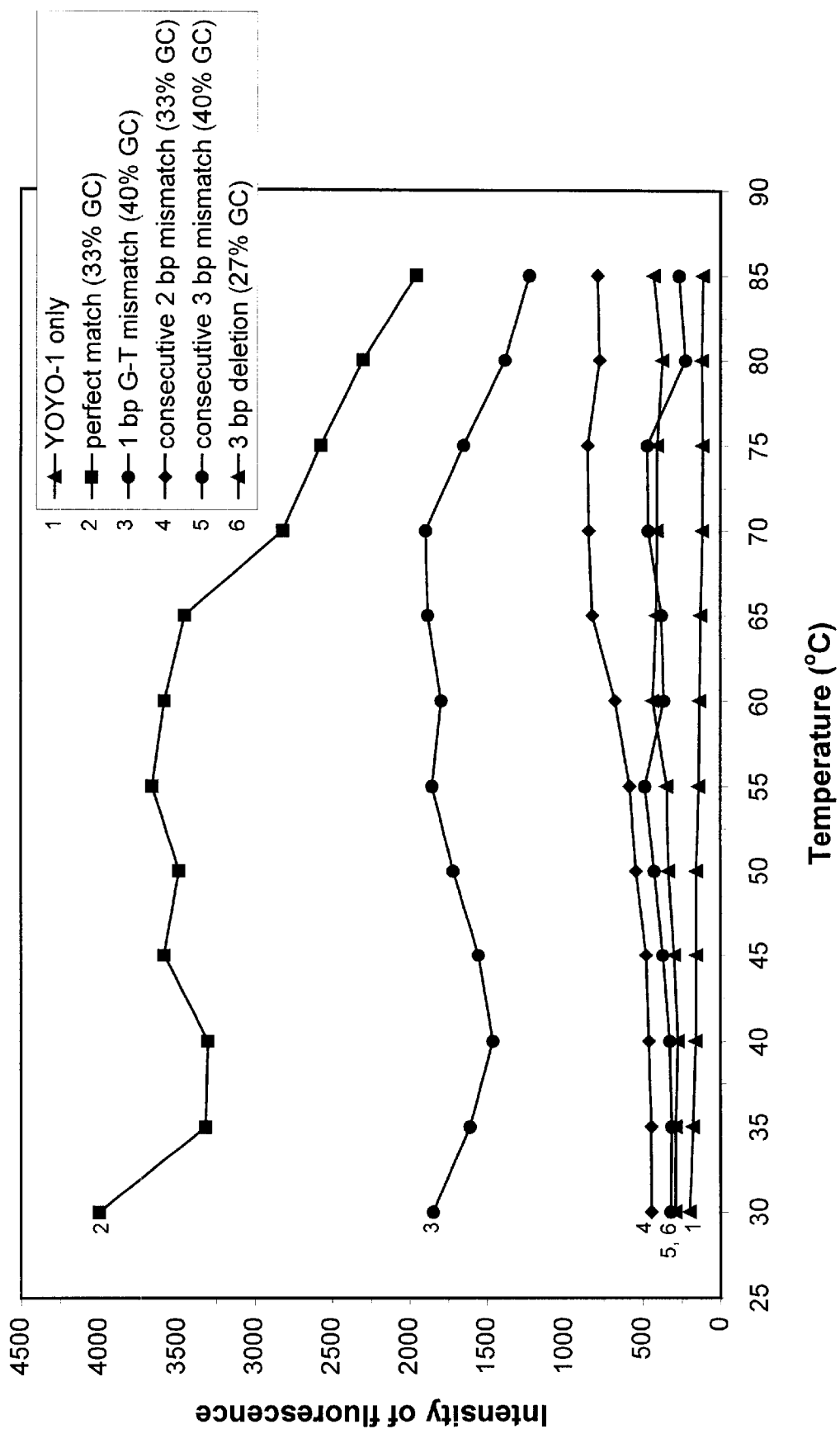
FIG. 5. 15-mer ssDNA to 50-mer dsDNA hybridization with YOYO-1 without prior denaturation

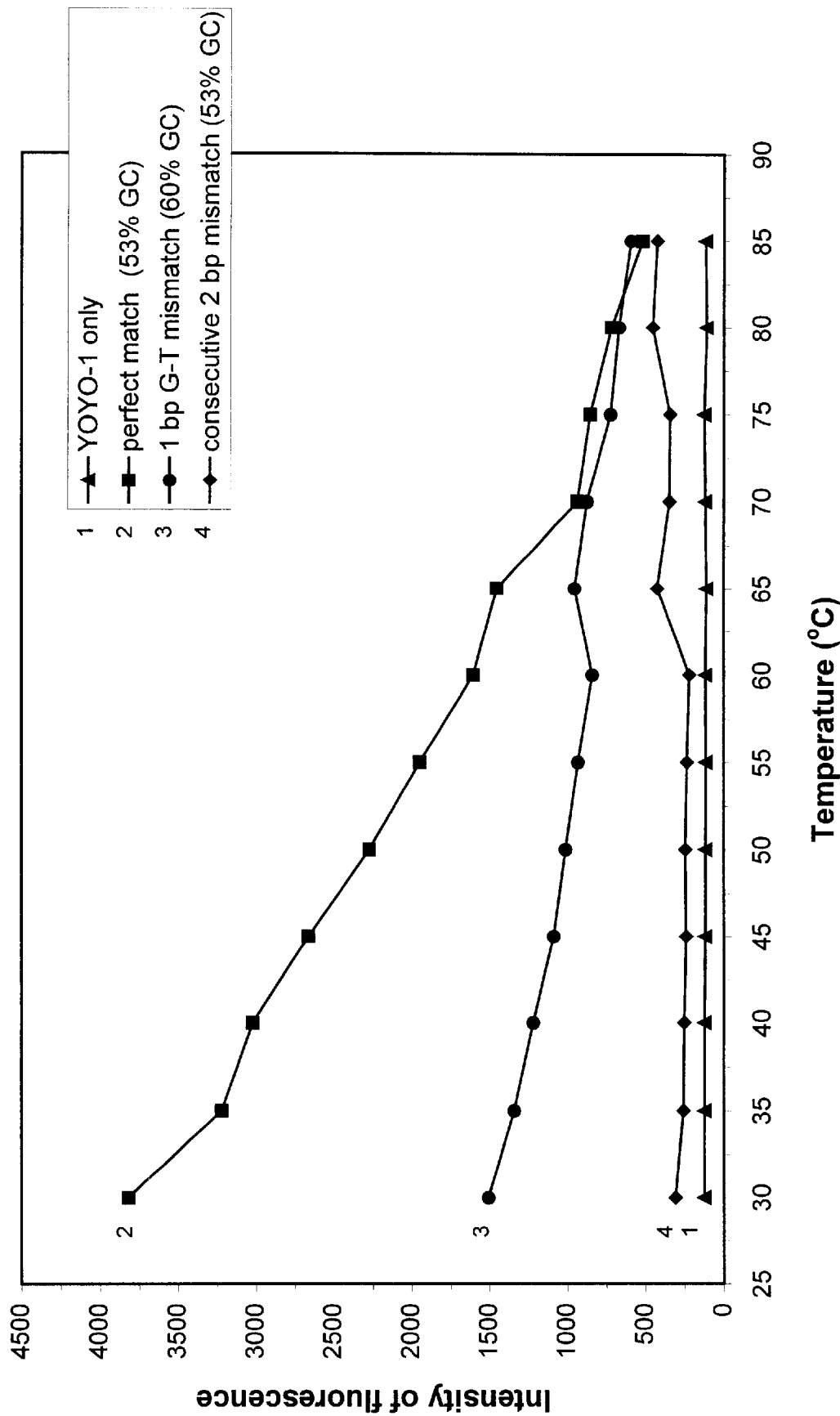
FIG. 6A. 15-mer ssDNA to 50-mer dsDNA hybridization with YOYO-1 without prior denaturation

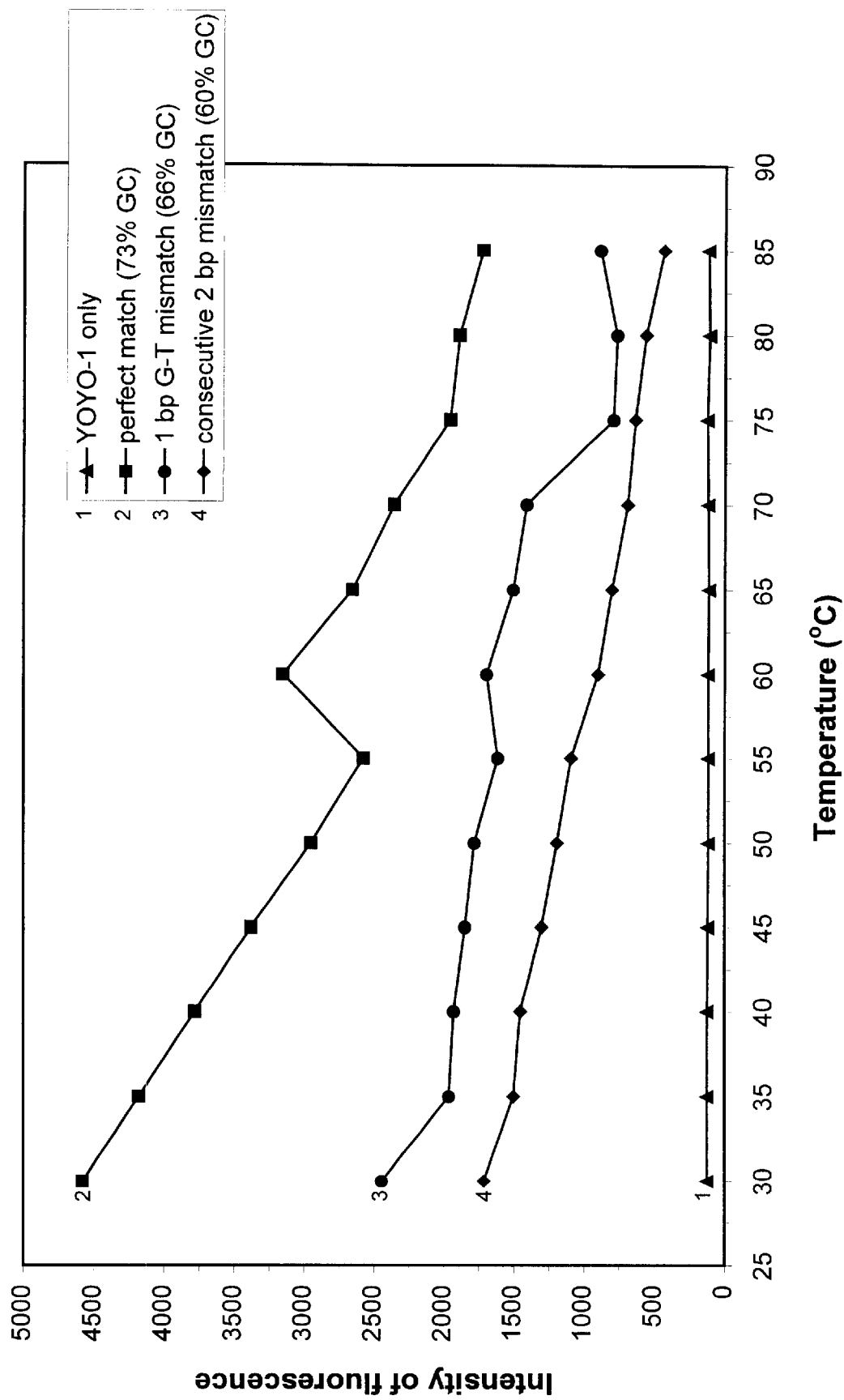
FIG. 6B. 15-mer ssDNA to 50-mer dsDNA hybridization with YOYO-1 without prior denaturation

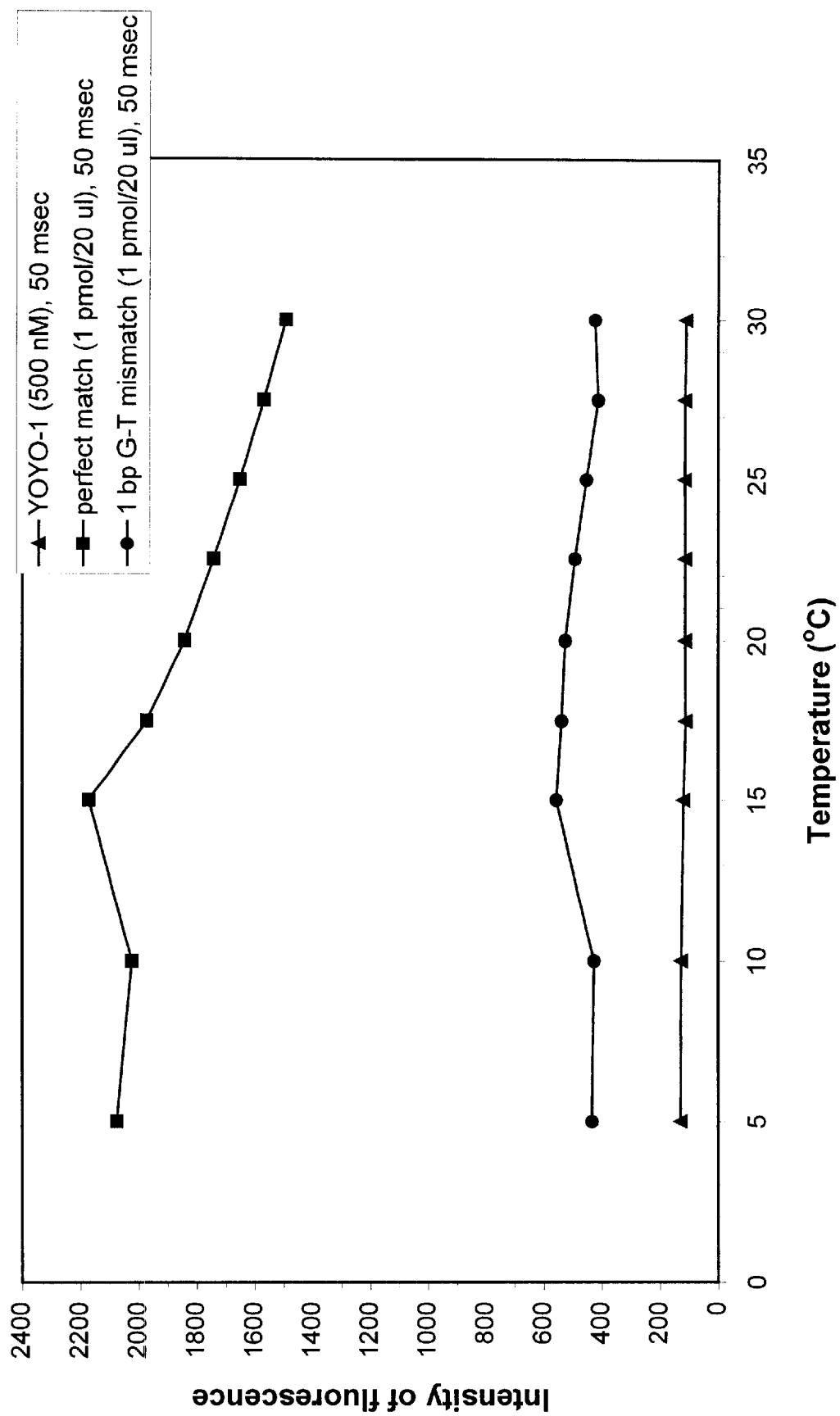
FIG. 7A. 15-mer ssDNA to 50-mer dsDNA hybridization with YOYO-1 without prior denaturation

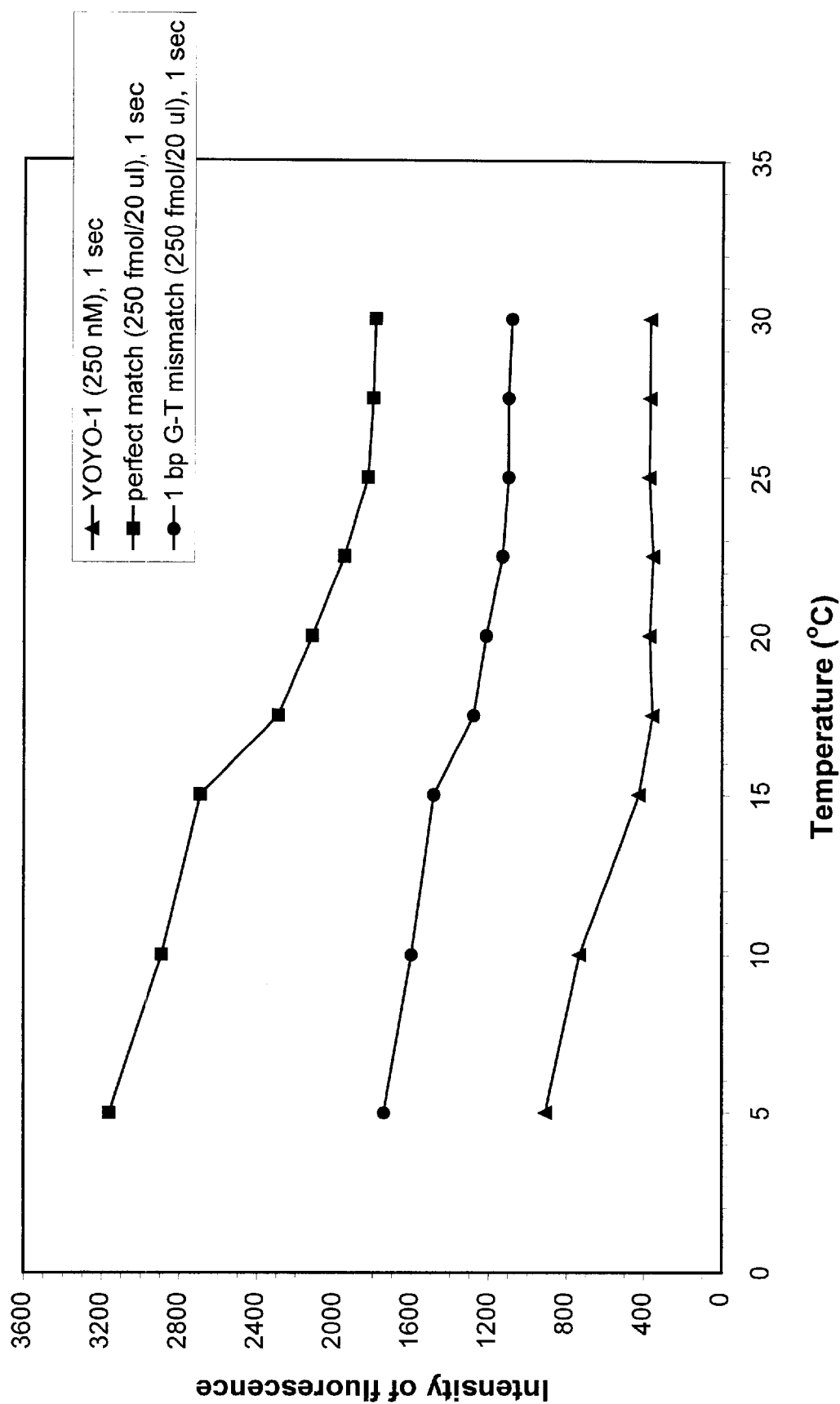
FIG. 7B. 15-mer ssDNA to 50-mer dsDNA hybridization with YOYO-1 without prior denaturation

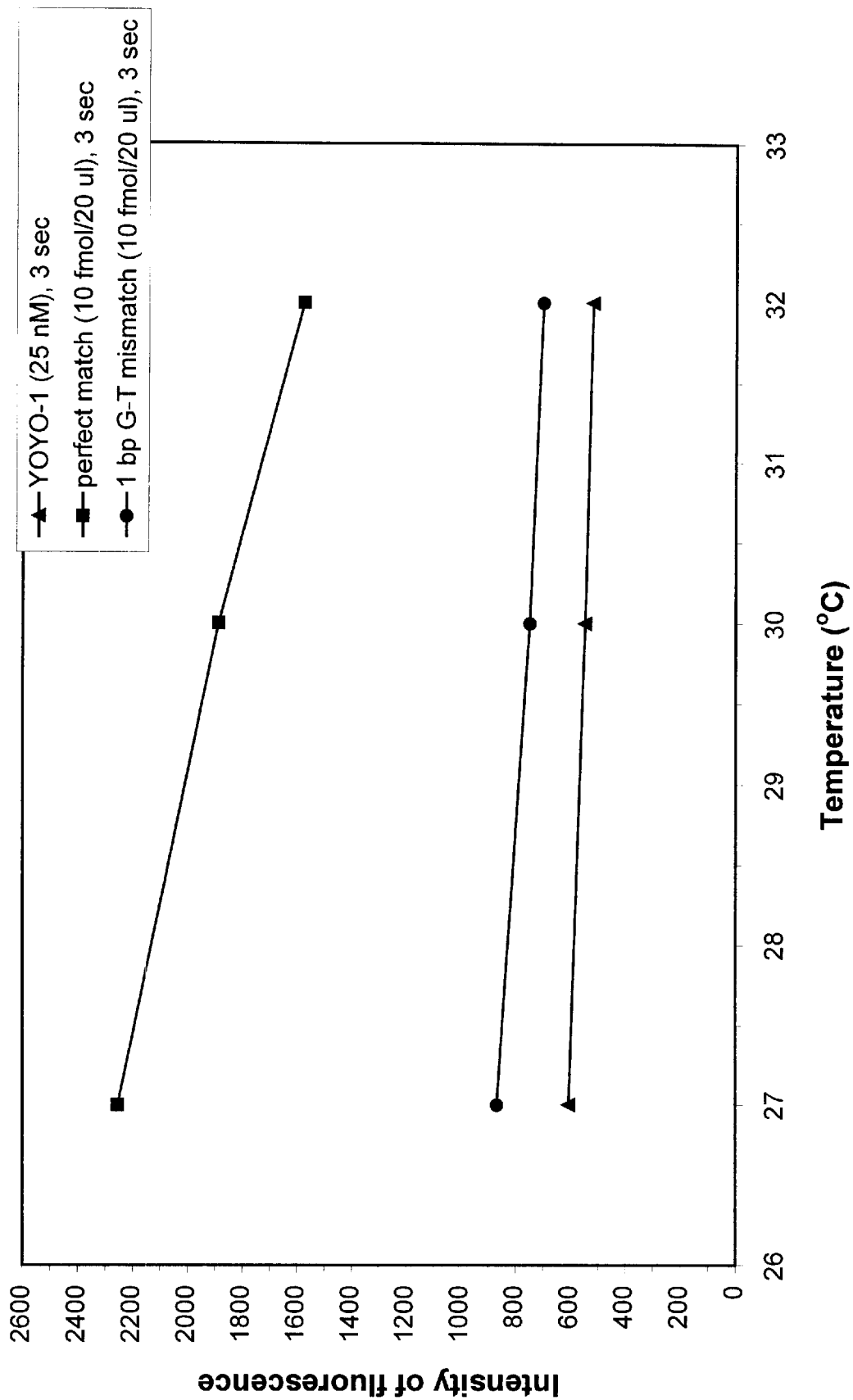

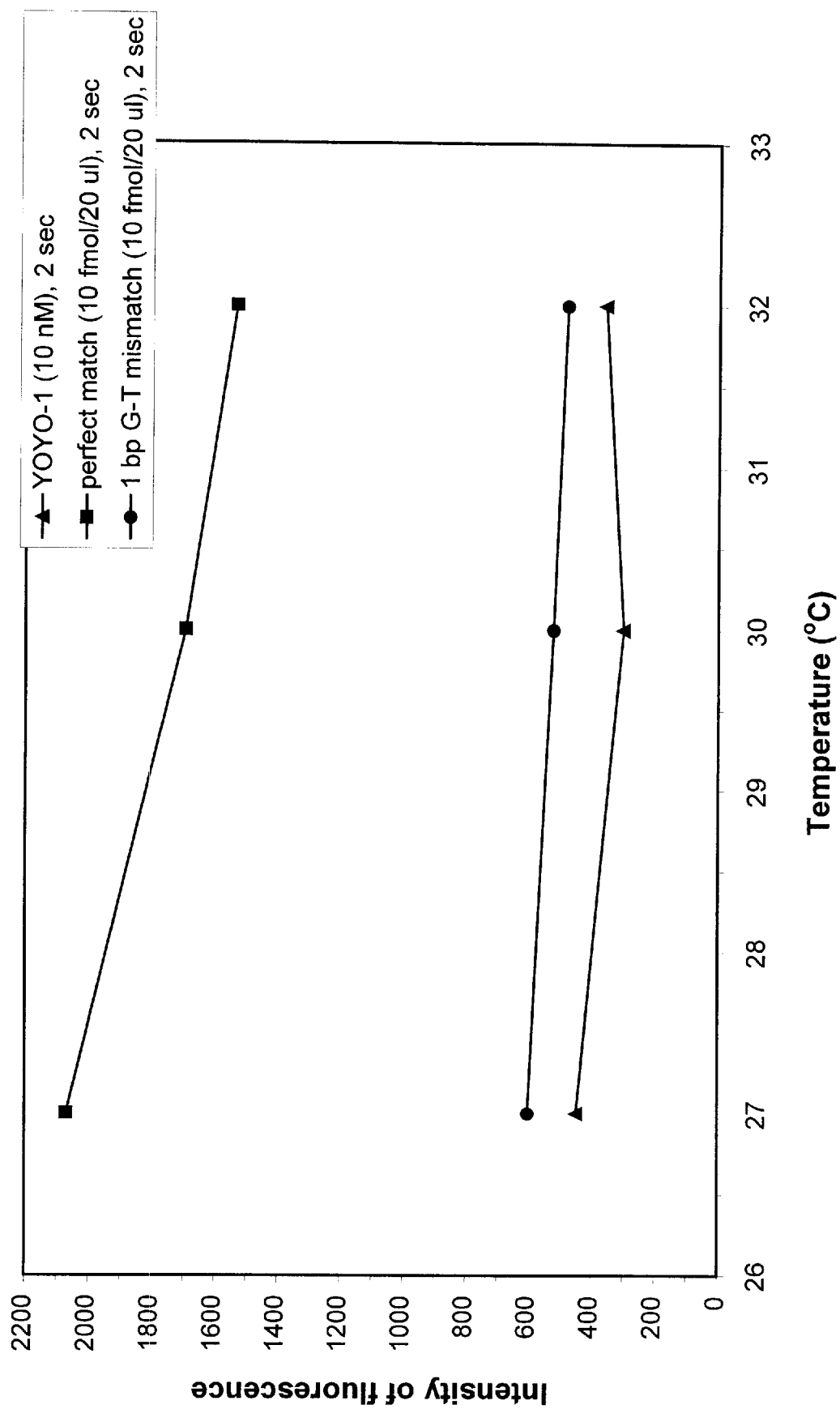
FIG. 8B. 15-mer ssDNA to 50-mer dsDNA hybridization with YOYO-1 without prior denaturation

SEQUENCE LISTING

```
<160> NUMBER OF SEQ ID NOS: 25

<210> SEQ ID NO 1
<211> LENGTH: 50
<212> TYPE: DNA
<213> ORGANISM: Artificial Sequence
<220> FEATURE:
<223> OTHER INFORMATION: Description of Artificial  Sequence: derived
      from exon 10 of the human cys tic fibrosis gene

<400> SEQUENCE: 1
tggcaccatt aaagaaaata tcatctttgg tgtttcctat gatgaatata              50

<210> SEQ ID NO 2
<211> LENGTH: 50
<212> TYPE: DNA
<213> ORGANISM: Artificial Sequence
<220> FEATURE:
<223> OTHER INFORMATION: Description of Artificial  Sequence: derived
      from exon 10 of the human cys tic fibrosis gene

<400> SEQUENCE: 2
tggcaccatt aaagaaaata tcgtctttgg tgtttcctat gatgaatata              50

<210> SEQ ID NO 3
<211> LENGTH: 50
<212> TYPE: DNA
<213> ORGANISM: Artificial Sequence
<220> FEATURE:
<223> OTHER INFORMATION: Description of Artificial  Sequence: derived
      from exon 10 of the human cys tic fibrosis gene

<400> SEQUENCE: 3
tggcaccatt aaagaaaata tactctttgg tgtttcctat gatgaatata              50

<210> SEQ ID NO 4
<211> LENGTH: 50
<212> TYPE: DNA
<213> ORGANISM: Artificial Sequence
<220> FEATURE:
<223> OTHER INFORMATION: Description of Artificial  Sequence: derived
      from exon 10 of the human cys tic fibrosis gene

<400> SEQUENCE: 4
tggcaccatt aaagaaaata tacgctttgg tgtttcctat gatgaatata              50
```

```
<210> SEQ ID NO 5
<211> LENGTH: 47
<212> TYPE: DNA
<213> ORGANISM: Artificial Sequence
<220> FEATURE:
<223> OTHER INFORMATION: Description of Artificial  Sequence: derived
      from exon 10 of the human cys tic fibrosis gene

<400> SEQUENCE: 5
tggcaccatt aaagaaaata tcattggtgt ttcctatgat gaatata              47

<210> SEQ ID NO 6
<211> LENGTH: 15
<212> TYPE: DNA
<213> ORGANISM: Artificial Sequence
<220> FEATURE:
<223> OTHER INFORMATION: Description of Artificial  Sequence: PNA probe

<400> SEQUENCE: 6
caccaaagat gatat                                                 15

<210> SEQ ID NO 7
<211> LENGTH: 15
<212> TYPE: DNA
<213> ORGANISM: Artificial Sequence
<220> FEATURE:
<223> OTHER INFORMATION: Description of Artificial  Sequence: PNA probe

<400> SEQUENCE: 7
tatagtagaa accac                                                 15

<210> SEQ ID NO 8
<211> LENGTH: 15
<212> TYPE: DNA
<213> ORGANISM: Artificial Sequence
<220> FEATURE:
<223> OTHER INFORMATION: Description of Artificial  Sequence: derived
      from exon 10 of the human cys tic fibrosis gene

<400> SEQUENCE: 8
atatcatctt tggtg                                                 15

<210> SEQ ID NO 9
<211> LENGTH: 15
<212> TYPE: DNA
<213> ORGANISM: Artificial Sequence
<220> FEATURE:
<223> OTHER INFORMATION: Description of Artificial  Sequence: derived
      from exon 10 of the human cys tic fibrosis gene

<400> SEQUENCE: 9
atatcttctt tggtg                                                 15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial  Sequence: derived
      from exon 10 of the human cys tic fibrosis gene

<400> SEQUENCE: 10
atatcatctt tcgtg                                                 15

<210> SEQ ID NO 11
<211> LENGTH: 15
```

```
<212> TYPE: DNA
<213> ORGANISM: Artificial Sequence
<220> FEATURE:
<223> OTHER INFORMATION: Description of Artificial Sequence: derived
      from exon 10 of the human cys tic fibrosis gene

<400> SEQUENCE: 11
atatcatgtt tggtg                                                    15

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: derived
      from exon 10 of the human cys tic fibrosis gene

<400> SEQUENCE: 12
atatcatcta tggtg                                                    15

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: derived
      from exon 10 of the human cys tic fibrosis gene

<400> SEQUENCE: 13
atatcatctc tggtg                                                    15

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: derived
      from exon 10 of the human cys tic fibrosis gene

<400> SEQUENCE: 14
atatcatctg tggtg                                                    15

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: derived
      from exon 10 of the human cys tic fibrosis gene

<400> SEQUENCE: 15
atatcgtctt tggtg                                                    15

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: derived
      from exon 10 of the human cys tic fibrosis gene

<400> SEQUENCE: 16
atatcatttt tggtg                                                    15

<210> SEQ ID NO 17
<211> LENGTH: 15
<212> TYPE: DNA
```

```
<213> ORGANISM: Artificial Sequence
<220> FEATURE:
<223> OTHER INFORMATION: Description of Artificial  Sequence: derived
      from exon 10 of the human cys tic fibrosis gene

<400> SEQUENCE: 17
atatcatctt ttgtg                                              15

<210> SEQ ID NO 18
<211> LENGTH: 50
<212> TYPE: DNA
<213> ORGANISM: Artificial Sequence
<220> FEATURE:
<223> OTHER INFORMATION: Description of Artificial  Sequence: derived
      from exon 10 of the human cys tic fibrosis gene

<400> SEQUENCE: 18
gagcaccatg acagacactg tcatctctgg tgtgtcctac gatgactctg         50

<210> SEQ ID NO 19
<211> LENGTH: 50
<212> TYPE: DNA
<213> ORGANISM: Artificial Sequence
<220> FEATURE:
<223> OTHER INFORMATION: Description of Artificial  Sequence: derived
      from exon 10 of the human cys tic fibrosis gene

<400> SEQUENCE: 19
gagcaccatg acagacactg tcgtctctgg tgtgtcctac gatgactctg         50

<210> SEQ ID NO 20
<211> LENGTH: 50
<212> TYPE: DNA
<213> ORGANISM: Artificial Sequence
<220> FEATURE:
<223> OTHER INFORMATION: Description of Artificial  Sequence: derived
      from exon 10 of the human cys tic fibrosis gene

<400> SEQUENCE: 20
gagcaccatg acagacactg tactctctgg tgtgtcctac gatgactctg         50

<210> SEQ ID NO 21
<211> LENGTH: 50
<212> TYPE: DNA
<213> ORGANISM: Artificial Sequence
<220> FEATURE:
<223> OTHER INFORMATION: Description of Artificial  Sequence: derived
      from exon 10 of the human cys tic fibrosis gene

<400> SEQUENCE: 21
gagcaccctc ccaggcacgg tcgtccctgg tgcgacctcc gacgagcgtg         50

<210> SEQ ID NO 22
<211> LENGTH: 50
<212> TYPE: DNA
<213> ORGANISM: Artificial Sequence
<220> FEATURE:
<223> OTHER INFORMATION: Description of Artificial  Sequence: derived
      from exon 10 of the human cys tic fibrosis gene

<400> SEQUENCE: 22
gagcaccctc ccaggcacgg tcatccctgg tgcgacctcc gacgagcgtg         50

<210> SEQ ID NO 23
<211> LENGTH: 50
<212> TYPE: DNA
<213> ORGANISM: Artificial Sequence
```

```
<220> FEATURE:
<223> OTHER INFORMATION: Description of Artificial  Sequence: derived
      from exon 10 of the human cys tic fibrosis gene

<400> SEQUENCE: 23
gagcaccctc ccaggcacgg tattccctgg tgcgacctcc gacgagcgtg              50

<210> SEQ ID NO 24
<211> LENGTH: 15
<212> TYPE: DNA
<213> ORGANISM: Artificial Sequence
<220> FEATURE:
<223> OTHER INFORMATION: Description of Artificial  Sequence: ss DNA
      probe

<400> SEQUENCE: 24
caccagagat gacag                                                   15

<210> SEQ ID NO 25
<211> LENGTH: 15
<212> TYPE: DNA
<213> ORGANISM: Artificial Sequence
<220> FEATURE:
<223> OTHER INFORMATION: Description of Artificial  Sequence: ss DNA
      probe

<400> SEQUENCE: 25
caccagggac gaccg                                                   15
```

FLUORESCENT INTENSITY ASSAY FOR DUPLEX AND TRIPLEX NUCLEIC ACID HYBRIDIZATION SOLUTION UTILIZING FLUORESCENT INTERCALATORS

BACKGROUND OF THE INVENTION

1. Field of Invention

The invention relates to methods of sequencing or assaying nucleic acids, and more particularly to methods of assaying triplex and duplex nucleic acid hybridization complexes employing fluorescent intensity measurements.

2. Description of Related Art

Fluorescent dyes have been used to detect and quantitate nucleic acids for decades. In their most basic form, fluorescent intensity-based assays have typically comprised contacting a target with a fluorophore-containing probe, removing any unbound probe from bound probe, and detecting fluorescence in the washed sample. Homogeneous assays improve upon such basic assays, in that the former do not require a washing step or the provision of a non-liquid phase support.

For example, U.S. Pat. No. 5,538,848 to Livak et al. and U.S. Pat. No. 4,220,450 to Maggio disclose homogeneous fluorescence-based assays of nucleotide sequences using oligonucleotide probes in solution. However, these patents require the use of a quenching agent in combination with a reporting agent, so as to distinguish between the signals generated by hybridized probes and unhybridized probes. Livak et al. also requires the use of enzymes in its disclosed method. Quenching agents and enzymes add complexity and expense to the methods.

U.S. Pat. No. 5,332,659 to Kidwell discloses a method for detecting nucleotide sequences in solution using probes comprising at least two fluorophore moieties. The fluorophores must be selected to electronically interact with each other when close enough to vary the wavelength dependence of their spectra. Unhybridized probes are much more flexible than probes hybridized to the target sequence, and consequently the two fluorophore moieties on each probe are more likely to be close to each other when the probe is unhybridized than when the probe is hybridized. Thus, a change in emission wavelength correlated with free probe can be monitored as an indication of the amount of free probe in the sample.

U.S. Pat. No. 5,846,729 to Wu et al. also discloses homogeneous fluorescence-based assays for nucleic acid hybridization.

Some assays have employed intercalating fluorophores to detect nucleic acid hybridization, based on the ability of such fluorophores to bind between strands of nucleic acid in a hybridization complex.

For example, U.S. Pat. No. 5,824,557 to Burke et al. discloses a method and kit for detecting and quantitating nucleic acid molecules. A preferred embodiment relies on the intercalation of a dye into a double-stranded nucleic acid helix or single-stranded nucleic acid. The dye fluoresces after intercalation and the intensity is a direct measurement of the amount of nucleic acid present in the sample. While the method of Burke et al. is purported to be useful for measuring the amount of nucleic acid in a sample, the non-specific binding between intercalator and nucleic acid upon which the method is based renders the method impractical for detecting specific binding, particularly under conditions where non-target nucleic acid duplexes are present.

U.S. Pat. No. 5,814,447 to Ishiguro et al. discloses an assay which is purported to improve upon assays that rely on non-specific interaction between intercalating agents and nucleic acid duplexes, such as Burke et al. and an earlier assay described by Ishiguro et al. in Japanese Patent Public Disclosure No. 237000/1993. The earlier development comprised adding an intercalating fluorochrome having a tendency to exhibit increased intensity of fluorescence when intercalated to a sample solution before a specific region of a target nucleic acid was amplified by PCR, and measuring the intensity of fluorescence from the reaction solution at given time intervals to detect and quantitate the target nucleic acid before amplification. The '447 patent attempted to improve upon the earlier development by providing an assay having improved specificity, characterized in that the probe is a single-stranded oligonucleotide labeled with an intercalating fluorochrome which is to be intercalated into a complementary binding portion between a target nucleic acid and a single-stranded oligonucleotide probe.

In addition to the aforementioned developments which detect fluorescent intensity, some have touted the advantages of fluorescent polarization assays. However, there are significant drawbacks to polarization-based assays. The degree of change in polarization as a function of binding can be unpredictable, and interpretation of data to conform inconsistent data to theoretical expectations can require more effort than is desirable in an analytical method, particularly when the method is to be automated.

Despite the foregoing developments, a need has continued to exist in the art for a simple, highly sensitive, effective and rapid method for analyzing interaction between nucleic acids and/or nucleic acid analogs.

All references cited herein are incorporated herein by reference in their entireties.

SUMMARY OF THE INVENTION

The invention provides a method for assaying binding, said method comprising:

providing a target comprising at least one nucleic acid sequence;

providing a probe comprising a nucleic acid or nucleic acid analog sequence imperfectly complementary to at least a portion of said target;

providing an intercalating agent, wherein either said probe or said intercalating agent comprises a fluorophore;

adding said probe, said target and said intercalating agent to a hybridization medium to provide a test sample;

irradiating said test sample with exciting radiation to cause said fluorophore to emit fluorescent radiation;

detecting an intensity of said fluorescent radiation, wherein said intensity is a direct indication of a binding affinity between said probe and said target; and determining from said intensity an extent of mismatching between said probe and said target.

BRIEF DESCRIPTION OF THE DRAWINGS

The invention will be described in conjunction with the following drawings in which like reference numerals designate like elements and wherein:

FIGS. 1A, 1B, 2, 3A, 3B, 4, 5, 6A, 6B, 7A, 7B, 8A and 8B are composite graphs of maximum fluorescent intensities plotted as a function of temperature for each sample analyzed.

DETAILED DESCRIPTION OF PREFERRED EMBODIMENTS

The invention provides a rapid, sensitive, environmentally friendly, and safe method for assaying binding between a target and a probe, wherein the target comprises a nucleic acid sequence or a nucleic acid analog sequence and the probe comprises a nucleic acid sequence or a nucleic acid analog sequence.

Unlike certain prior art assays, the invention not only detects the presence of hybridization, but also provides qualitative and quantitative information regarding the nature of hybridization between a probe and target. Thus, the invention enables the practitioner to distinguish among a perfect match, a one base pair mismatch, a two base pair mismatch, a three base pair mismatch, a one base pair deletion, a two base pair deletion and a three base pair deletion.

Embodiments of the invention comprise calibrating the fluorescent intensity measured for a first probe-target mixture against intensities exhibited by other probes combined with the same target and the same intercalating agent, wherein each of the other probes differs from the first probe by at least one base. The fluorescent intensity detected in the method of the invention increases with increasing binding affinity between the probe and target. The instant method does not require the measurement of the polarization of fluorescence, unlike fluorescent anisotropy methods.

A calibration curve can be generated, wherein the intensity is a function of the binding affinity between the target and probe. As the binding affinity between the target and a plurality of different probes varies with the number of mismatched bases, the nature of the mismatch (A-G vs. A-C vs. T-G vs. T-C, etc.), the location of the mismatch(es) within the hybridization complex, etc., the assay of the invention can be used to sequence the target.

The invention enables quantifying the binding affinity between probe and target. Such information can be valuable for a variety of uses, including designing antisense drugs with optimized binding characteristics.

Unlike prior art methods, the assay of the invention is preferably homogeneous. The assay can be conducted without separating the probe-target complex from the free probe and target prior to the fluorescent intensity detecting. The assay does not require a gel separation step, thereby allowing a great increase in testing throughput. Quantitative analyses are simple and accurate. Further, the assay is preferably conducted in a homogeneous solution, eliminating the requirement for separation of bound complexes from unbound probes, by either filtration and numerous washing steps or by gel electrophoresis. Consequently the binding assay saves a lot of time and expense, and can be easily automated. Furthermore, it enables binding variables such as buffer, pH, ionic concentration, temperature, incubation time, relative concentrations of probe and target sequences, intercalator concentration, length of target sequences, length of probe sequences, and possible cofactor requirements to be rapidly determined.

Moreover, the inventive assay is preferably conducted without providing a signal quenching agent on the target or on the probe.

Preferred embodiments of the invention specifically detect triplex hybridization between the probe and the double-stranded target, thus obviating the need to denature the target. While PNA probes have been known to form triplexes with certain classes of targets (see, e.g., Egholm et al., 365 Nature 566 (1993), and Tomac et al., 118 J. Am. Chem. Soc. 5544 (1996)), the inventors were surprised that they were able to specifically assay triplexes formed between single-stranded nucleic acid (e.g., ssDNA and RNA) probes and double-stranded nucleic acid (e.g., dsDNA) targets.

Suitable probes for use in the inventive assay include, e.g., ssDNA, RNA, PNA and other nucleic acid analogs having uncharged backbones. Probe sequences having any length from 8 to 20 bases are preferred since this is the range within which the smallest unique DNA sequences of prokaryotes and eukaryotes are found. Probes of 12 to 18 bases are particularly preferred since this is the length of the smallest unique sequences in the human genome. In embodiments, probes of 6–30 bases are preferred, with 15 bases being most preferred. However, a plurality of shorter probes can be used to detect a nucleotide sequence having a plurality of non-unique target sequences therein, which combine to uniquely identify the nucleotide sequence.

The invention does not require the use of radioactive probes, which are hazardous, tedious and time-consuming to use, and need to be constantly regenerated. Probes of the invention are preferably safe to use and stable for years. Accordingly, probes can be made or ordered in large quantities and stored.

The inventors were also surprised to discover that parallel PNA probes outperform more conventionally synthesized anti-parallel PNA probes. When the nucleic acid target sequences were more than three-fold longer than the PNA probes, the parallel and antiparallel PNA probes were equally efficient in distinguishing between perfectly matched nucleic acid hybridization complexes and those containing various one base pair, two base pair or three base pair mismatches. However, when the target DNA sequences were the same length as the PNA probe sequences (i.e., 15 nucleotides long), parallel PNA probes were much preferred than antiparallel PNA probes, because of greater differences in observed fluorescent intensities between perfectly matched complexes and one or two base pair mismatched complexes.

Although the exact mechanism by which parallel PNA probes are preferred under such conditions is not known, these observations suggest that the mismatched parallel PNA:DNA hybridization complexes are less stable than the analogous mismatched antiparallel PNA:DNA hybrids, resulting in less intercalation of the nucleic acid intercalator and hence lower observed fluorescent intensity values.

It is preferred that the probe and target be unlabeled, but in alternative embodiments, there is an intercalating agent covalently bound to the probe. In such embodiments, the intercalating agent is preferably bound to the probe at either end.

In other embodiments, the intercalating agent is not covalently bound to the probe, although it can insert itself between the probe and target during the assay, in a sense bonding to the probe in a non-covalent fashion.

Preferred intercalating agents for use in the invention include, e.g., YOYO-1, TOTO-1, ethidium bromide, ethidium homodimer-1, ethidium homodimer-2 and acridine. In general, the intercalating agent is a moiety that is able to intercalate between strands of a duplex and/or a triplex nucleic acid complex. In preferred embodiments, the intercalating agent (or a component thereof) is essentially non-fluorescent in the absence of nucleic acids and fluoresces when intercalated and excited by radiation of an appropriate wavelength, exhibiting a 100-fold to 10,000-fold enhancement of fluorescence when intercalated within a duplex or triplex nucleic acid complex.

In alternative embodiments, the intercalating agent may exhibit a shift in fluorescent wavelength upon intercalation and excitation by radiation of an appropriate wavelength. The exact fluorescent wavelength may depend on the structure of the nucleic acid that is intercalated, for example, DNA vs. RNA, duplex vs. triplex, etc.

The excitation wavelength is selected (by routine experimentation and/or conventional knowledge) to correspond to this excitation maximum for the fluorophore being used, and is preferably 200 to 1000 nm. Intercalating agents are preferably selected to have an emission wavelength of 200 to 1000 nm. In preferred embodiments, an argon ion laser is used to irradiate the fluorophore with light having a wavelength in a range of 400 to 540 nm, and fluorescent emission is detected in a range of 500 to 750 nm.

The assay of the invention can be performed over a wide variety of temperatures, such as, e.g., from 5 to 85° C. Certain prior art assays require elevated temperatures, adding cost and delay to the assay. On the other hand, the invention can be conducted at room temperature or below (e.g., at a temperature below 25° C.).

The reliability of the invention is independent of a guanine and cytosine content in said target. Since G-C base pairs form three hydrogen bonds, while A-T base pairs form only two hydrogen bonds, target and probe sequences with a higher G or C content are more stable, possessing higher melting temperatures. Consequently, base pair mismatches that increase the GC content of the hybridized probe and target region above that present in perfectly matched hybrids may offset the binding weakness associated with a mismatched probe. Hybridization complexes containing every possible base pair mismatch between the probe and the target proved to be more unstable than perfectly matched hybrids, always resulting in lower fluorescent intensities than did perfectly complementary hybrids.

The inventive assay is extremely sensitive, thereby obviating the need to conduct PCR amplification of the target. For example, it is possible to assay a test sample having a volume of about 20 microliters, which contains about 10 femtomoles of target and about 10 femtomoles of probe. Embodiments of the invention are sensitive enough to assay targets at a concentration of $5 \times 10^{-9}$ M, preferably at a concentration of not more than $5 \times 10^{-10}$ M. Embodiments of the invention are sensitive enough to employ probes at a concentration of $5 \times 10^{-9}$ M, preferably at a concentration of not more than $5 \times 10^{-10}$ M. It should go without saying that the foregoing values are not intended to suggest that the method cannot detect higher concentrations.

The hybridization medium can be any conventional medium known to be suitable for preserving nucleotides. See, e.g., Sambrook et al., "Molecular Cloning: A Lab Manual," Vol. 2 (1989). For example, the liquid medium can comprise nucleotides, water, buffers and standard salt concentrations.

Hybridization between complementary bases occurs under a wide variety of conditions having variations in temperature, salt concentration, electrostatic strength, and buffer composition. Examples of these conditions and methods for applying them are known in the art.

It is preferred that hybridization complexes be formed at a temperature of about 15° C. to about 25° C. for about 1 minute to about 5 minutes. Longer reaction times are not required, but incubation for several hours will not adversely affect the hybridization complexes.

Provided that a suitable fluorescent intercalating agent is included in the reaction mixture (as discussed earlier), under the vast majority of cases, other facilitating reagents are not required. However, it is possible to facilitate hybridization in solution by using certain reagents. Preferred examples of these reagents include single stranded binding proteins such as Rec A protein, T4 gene 32 protein, *E. coli* single stranded binding protein, major or minor nucleic acid groove binding proteins, divalent ions, polyvalent ions, viologen and intercalating substances such as ethidium bromide, actinomycin D, psoralen, and angelicin. Such facilitating reagents may prove useful in extreme operating conditions, for example, under abnormal pH levels or extremely high temperatures.

The inventive assay can be used to, e.g., identify accessible regions in folded nucleotide sequences, to determine the number of mismatched base pairs in a hybridization complex, and to map genomes.

The invention will be illustrated in more detail with reference to the following Examples, but it should be understood that the present invention is not deemed to be limited thereto.

EXAMPLES

Example 1

Sense and antisense 50-mer ssDNA target sequences, derived from exon 10 of the human cystic fibrosis gene (Nature 380, 207 (1996)) were synthesized on a DNA synthesizer (Expedite 8909, PerSeptive Biosystems) and purified by HPLC. Equimolar amounts of complementary oligonucleotides were denatured at 95° C. for 10 min and allowed to anneal gradually as the temperature cooled to 21° C. over 1.5 hours. DsDNA oligonucleotides were dissolved in ddH$_2$O at a concentration of 1 pmole/µl.

The sense strand of the wild-type target DNA had the following sequence (SEQ ID NO:1): 5'-TGG CAC CAT TAA AGA AAA TAT CAT CTT TGG TGT TTC CTA TGA TGA ATA TA-3'.

The antisense strand of the wild-type target DNA had the following sequence (SEQ ID NO:1): 5'-TAT ATT CAT CAT AGG AAA CAC CAA AGA TGA TAT TTT CTT TAA TGG TGC CA-3'.

A 50-mer mutant dsDNA target sequence was prepared to be identical to the wild-type target DNA (SEQ ID NO:1) except for a one base pair mutation (underlined) at amino acid position 507 at which the wild-type sequence CAT was changed to C<u>G</u>T.

The sense strand of this 50-mer target sequence had the following sequence (SEQ ID NO:2): 5'-TGG CAC CAT TAA AGA AAA TAT C<u>G</u>T CTT TGG TGT TTC CTA TGA TGA ATA TA-3'.

The antisense strand of this 50-mer target sequence had the following sequence (SEQ ID NO:2): 5'-TAT ATT CAT CAT AGG AAA CAC CAA AGA <u>C</u>GA TAT TTT CTT TAA TGG TGC CA-3'.

A 50-mer mutant dsDNA target sequence was prepared to be identical to wild-type target DNA (SEQ ID NO:1) except for a consecutive two base pair mutation (underlined) at amino acid positions 506 and 507 at which the wild-type sequence CAT was changed to <u>AC</u>T.

The sense strand of this target sequence had the following sequence (SEQ ID NO:3): 5'-TGG CAC CAT TAA AGA AAA TAT <u>AC</u>T CTT TGG TGT TTC CTA TGA TGA ATA TA-3'.

The antisense strand of this target sequence had the following sequence (SEQ ID NO:3): 5'-TAT ATT CAT CAT AGG AAA CAC CAA AGA <u>GT</u>A TAT TTT CTT TAA TGG TGC CA-3'.

A 50-mer mutant dsDNA target sequence was prepared to be identical to wild-type target DNA (SEQ ID NO:1) except for a consecutive three base pair mutation (underlined) at amino acid positions 506 and 507 at which the wild-type sequence CAT was changed to ACG.

The sense strand of this target sequence had the following sequence (SEQ ID NO:4): 5'-TGG CAC CAT TAA AGA AAA TAT ACG CTT TGG TGT TTC CTA TGA TGA ATA TA-3'.

The antisense strand of this target sequence had the following sequence (SEQ ID NO:4): 5'-TAT ATT CAT CAT AGG AAA CAC CAA AGC GTA TAT TTT CTT TAA TGG TGC CA-3'.

A 47-mer mutant dsDNA target sequence was prepared to be identical to wild-type target DNA (SEQ ID NO:1) except for a consecutive three base pair deletion (indicated by an ellipsis) at amino acid positions 507 and 508 at which the wild-type sequence CTT is deleted.

The sense strand of this 47-mer target sequence had the following sequence (SEQ ID NO:5): 5¹-TGG CAC CAT TAA AGA AAA TAT CAT . . . TGG TGT TTC CTA TGA TGA ATA TA-3'.

The antisense strand of this 47-mer target sequence had the following sequence (SEQ ID NO:5): 5'-TAT ATT CAT CAT AGG AAA CAC CA . . . A TGA TAT TTT CTT TAA TGG TGC CA-31.

The PNA probes used in the Examples were synthesized, HPLC purified and confirmed by mass spectroscopy by Commonwealth Biotechnologies, Inc. (Richmond, Va., USA). PNA probes were first dissolved in 0.1% TFA (trifluoroacetic acid) to a concentration of 10 mg/ml, and then diluted to 1 mg/ml by the addition of ddH$_2$O. Final PNA stock solutions were prepared in ddH$_2$O at a concentration of 1 pmole/µl.

Probe No. 1 was a 15-mer antiparallel PNA probe designed to be completely complementary to a 15 nucleotide segment of the sense strand of the 50-mer wild-type target DNA (SEQ ID NO:1), overlapping amino acid positions 505 to 510 (Nature 380, 207 (1996)). The probe had the following structure (SEQ ID NO:6): 5'-H-CAC CAA AGA TGA TAT-Lys-CONH$_2$-3'.

Probe No. 2 was a 15-mer PNA probe identical in sequence to Probe No. 1, but was in the parallel orientation, instead of the antiparallel orientation. The probe had the following structure (SEQ ID NO:7):

5'-H-TAT AGT AGA AAC CAC-Lys-CONH$_2$-3'.

Each hybridization reaction mixture (80µl) contained the following: 4 pmoles of target dsDNA, 4 pmoles of PNA probe, 0.5×TBE and 500 nM of the DNA intercalator YOYO-1 (Molecular Probes, Eugene, Oreg., USA). The reaction mixtures were incubated at 95° C. for 5–10 minutes to allow denaturation, and then maintained at 80° C. until assayed. Samples were placed into a quartz cuvette, irradiated with an argon ion laser beam having a wavelength of 488 nm and monitored repeatedly for fluorescent emission as the temperature decreased with time. Concurrent temperature measurements were achieved by a software-controlled temperature probe placed directly into each sample. The maximum fluorescent intensity occurred at a wavelength of 540 nm, indicative of intercalation of YOYO-1 in the PNA:DNA hybrids. Maximum fluorescent intensities were plotted as a function of temperature for each sample analyzed.

The fluorescent intensities observed when no DNA or PNA was present (YOYO-1 only), or when wild-type SEQ ID NO:1, mutant SEQ ID NO:2 or mutant SEQ ID NO:3 were reacted with antiparallel PNA Probe No. 1 or parallel PNA Probe No. 2 are shown in FIGS. 1A and 1B, respectively. SsDNA:PNA hybrids consisting of perfectly complementary sequences (SEQ ID NO:1+Probe No. 1) allowed maximum intercalation of YOYO-1, yielding the highest fluorescent intensities, which increased as the temperature decreased (FIG. 1A). The fluorescent intensities for a one base pair mismatched ssDNA:PNA hybrid (SEQ ID NO:2+ Probe No. 1) and a two base pair mismatched ssDNA:PNA hybrid (SEQ ID NO:3 +Probe No. 1) were 81% and 89% lower, respectively, than the perfectly matched ssDNA:PNA hybrid at 60° C. (FIG. 1A). Similarly, when parallel PNA Probe No. 2 was hybridized to the target DNA sequences, the one and two base pair mismatched ssDNA:PNA hybrids exhibited fluorescent intensities that were 70% and 86% lower, respectively, than the perfectly complementary ssDNA:PNA hybrid (SEQ ID NO:1+Probe No. 2) at 60° C. (FIG. 1B). As the degree of mismatch between the probe and the target increased, the level of intercalation by YOYO-1 diminished and hence the level of fluorescent intensity decreased. This relationship held irrespective of whether an antiparallel or parallel PNA probe was used.

Interestingly, when the target DNA sequences were the same length as the PNA probe sequences (i.e., 15 nucleotides long), parallel PNA probes were much preferred than antiparallel PNA probes, because of greater differences in observed fluorescent intensities between perfectly matched complexes and one or two base pair mismatched complexes (data not shown).

Although the exact mechanism by which parallel PNA probes are preferred under such conditions is not known, these observations suggest that the mismatched parallel PNA:DNA hybridization complexes are less stable than the analogous mismatched antiparallel PNA:DNA hybrids, resulting in less intercalation of the nucleic acid intercalator and hence lower observed fluorescent intensity values.

Example 2

FIG. 2 demonstrates that the hybridization assay of the invention can also discriminate between perfectly matched ssDNA:PNA hybrids and those containing 1, 2 or 3 bp mismatches, as well as a 3 bp deletion, when a parallel PNA probe is employed. The assay conditions were identical to those described in Example 1. The fluorescent intensities for a 1 bp mismatched ssDNA:PNA hybrid (SEQ ID NO:2+ Probe No. 2), a consecutive 2 bp mismatch (SEQ ID NO:3+Probe No. 2), a consecutive 3 bp mismatch (SEQ ID NO:4+ Probe No. 2) and a 3 bp deletion (SEQ ID NO:5+ Probe No. 2) were 41%, 71%, 87% and 95% lower, respectively, than the perfectly matched ssDNA:PNA hybrid (SEQ ID NO:1+Probe No. 2) at 60° C. As the temperature decreased from 70° C. to 60° C., the degree of discrimination between perfect match and the various base pair mismatches increased. As in Example 1, increasing the degree of mismatch between the probe and the target resulted in progressively diminished levels of fluorescent intensity. Moreover, this pattern of fluorescence was consistent even when the mutant sequences displayed a percent GC content higher than that of the wild-type sequence (FIG. 2).

When a parallel PNA probe was used, separated 2 bp mismatches (wherein two 1 bp mismatches were separated by 3 base pairs) resulted in slightly lower fluorescent intensities than consecutive 2 bp mismatches (data not shown). Similarly, separated 3 bp mismatches (wherein three 1 bp mismatches were separated by 3 base pairs each) yielded slightly lower fluorescent intensities than consecutive 3 bp mismatches (data not shown). These results suggest that separated base pair mismatches are more disruptive of ssDNA:PNA hybrid formation than consecutive base pair mismatches.

Example 3

SEQ ID NO:8 was a 15-mer dsDNA target sequence derived from SEQ ID NO:1, designed to be completely complementary to Probe No. 1. SEQ ID NO:9 to SEQ ID NO:17 were 15-mer mutant dsDNA target sequences identical to wild-type SEQ ID NO:8 except for a one base pair mutation (underlined). Sense and antisense 15-mer ssDNA sequences were synthesized, purified and annealed as above. DsDNA oligonucleotides were dissolved in ddH$_2$O at a concentration of 1 pmole/µl.

The sequence for the sense strand of the wild-type target DNA (SEQ ID NO:8) was: 5'-ATA TCA TCT TTG GTG-3'.

The sequence for the antisense strand of the wild-type target DNA (SEQ ID NO:8) was: 5'-CAC CAA AGA TGA TAT-3'.

The sequence for the sense strand of the mutant target DNA (SEQ ID NO:9) was: 51-ATA TCT TCT TTG GTG-3'.

The sequence for the antisense strand of the mutant target DNA (SEQ ID NO:9) was: 5'-CAC CAA AGA <u>A</u>GA TAT-3'.

The sequence for the sense strand of the mutant target DNA (SEQ ID NO:10) was: 5'-ATA TCA TCT TT<u>C</u> GTG-3'.

The sequence for the antisense strand of the mutant target DNA (SEQ ID NO:10) was: 5'-CAC <u>G</u>AA AGA TGA TAT-3'.

The sequence for the sense strand of the mutant target DNA (SEQ ID NO:11) was: 5'-ATA TCA T<u>G</u>T TTG GTG-3'.

The sequence for the antisense strand of the mutant target DNA (SEQ ID NO:11) was: 5'-CAC CAA A<u>C</u>A TGA TAT-3'.

The sequence for the sense strand of the mutant target DNA (SEQ ID NO:12) was: 5'-ATA TCA TCT <u>A</u>TG GTG-3'.

The sequence for the antisense strand of the mutant target DNA (SEQ ID NO:12) was: 5'-CAC CA<u>T</u> AGA TGA TAT-3'.

The sequence for the sense strand of the mutant target DNA (SEQ ID NO:13) was: 5'-ATA TCA TCT <u>C</u>TG GTG-3'.

The sequence for the antisense strand of the mutant target DNA (SEQ ID NO:13) was: 5'-CAC CA<u>G</u> AGA TGA TAT-3'.

The sequence for the sense strand of the mutant target DNA (SEQ ID NO:14) was: 5'-ATA TCA TCT <u>G</u>TG GTG-3'.

The sequence for the antisense strand of the mutant target DNA (SEQ ID NO:14) was: 5'-CAC CA<u>C</u> AGA TGA TAT-3'.

The sequence for the sense strand of the mutant target DNA (SEQ ID NO:15) was: 5'-ATA TC<u>G</u> TCT TTG GTG-3'.

The sequence for the antisense strand of the mutant target DNA (SEQ ID NO:15) was: 5'-CAC CAA AGA <u>CGA</u> TAT-3'.

The sequence for the sense strand of the mutant target DNA (SEQ ID NO:16) was: 5'-ATA TCA T<u>TT</u> TTG GTG-3'.

The sequence for the antisense strand of the mutant target DNA (SEQ ID NO:16) was: 5'-CAC CAA A<u>AA</u> TGA TAT-3'.

The sequence for the sense strand of the mutant target DNA (SEQ ID NO:17) was: 5'-ATA TCA TCT TT<u>T</u> GTG-3'.

The sequence for the antisense strand of the mutant target DNA (SEQ ID NO:17) was: 5'-CAC <u>A</u>AA AGA TGA TAT-3'.

The specificity of the hybridization assay was further tested by reacting parallel PNA Probe No. 2 with a 15-mer wild-type target dsDNA (SEQ ID NO:8) and various 15-mer 1 bp mutated target dsDNAs (SEQ ID NO:9 to SEQ ID NO:17), that would generate every type of 1 bp mismatch possible (FIG. 3). The assay conditions were identical to those described in Example 1.

The highest fluorescent intensities were achieved with ssDNA:PNA hybrids consisting of perfectly complementary sequences, at all temperatures tested. Fluorescence increased as the temperature decreased. SsDNA:PNA hybrids that resulted in 1 bp T-T, C-C, G-G, A-A, C-A, G-A, G-T and C-T mismatches all yielded fluorescent intensities lower than that observed for perfectly matched ssDNA:PNA hybrids (FIGS. 3A and 3B). The fluorescent intensities for the 1 bp mismatches ranged from 64% to 96% lower, and 57% to 95% lower than those observed for the perfect match at 55° C. and 75° C., respectively. The variability in the fluorescent intensities observed between the various 1 bp mismatches depended more on the particular base pair mismatch than the change in percent GC content of the mutant sequences, when a parallel PNA probe was used (FIG. 3). When antiparallel PNA Probe No. 1 was tested in a similar experiment, the differences in fluorescent intensities observed between the perfect match and the various 1 bp mismatches were less dramatic than those achieved with the parallel PNA Probe No. 2 and seemed to be influenced by temperature (data not shown). The assay produced best results between 40° C. and 60° C., when an antiparallel PNA probe was used. A parallel PNA probe is therefore preferred when the target DNA sequences are the same length as the PNA probe sequences.

The results of FIG. 3 confirmed the reliability of the hybridization assay to identify all possible 1 bp mismatches with great accuracy.

Example 4

The hybridization assays in Examples 1 to 3 were performed after denaturation of the dsDNA target sequences and measured ssDNA:PNA hybrid formation at temperatures above the melting point ($T_m$) of the dsDNA targets. This example demonstrates the reliability of the assay of the invention to differentiate between perfect matches and base pair mismatches without requiring prior denaturation.

The hybridization reaction mixture (120 µl) contained the following: 6 pmoles of target dsDNA, 6 pmoles of parallel PNA Probe No. 2, 0.5×TBE and 500 nM of the DNA intercalator YOYO-1. Although the reaction volume was slightly greater than that in Examples 1 to 3, the DNA, PNA and YOYO-1 amounts were adjusted accordingly to maintain constant concentrations of samples. Identical results were obtained when the reaction volume was 40 µl, 80 µl or 120 µl. The reaction mixtures were incubated at room temperature (21° C.) for 5 minutes, placed into a quartz cuvette, irradiated with an argon ion laser beam having a wavelength of 488 nm and monitored repeatedly for fluorescent emission as the temperature increased with time, in a heated chamber. Concurrent temperature measurements of the samples were achieved by a software-controlled temperature probe placed directly into each sample. Maximum fluorescent intensities were plotted as a function of temperature for each sample analyzed.

FIG. 4 illustrates that even in the absence of prior denaturation, the highest fluorescent intensities were achieved when the wild-type 50-mer dsDNA target sequence (SEQ ID NO:1) was reacted with the 15-mer parallel PNA Probe No. 2 from 30° C. to 85° C. At temperatures below 65° C., the $T_m$ of the 50-mer wild-type dsDNA, dsD- NA:PNA triplexes were formed. As the temperature increased above 65° C., the triplex structures converted to ssDNA:PNA duplexes. Clearly YOYO-1 was able to intercalate efficiently in both the triplex and duplex structures. Consequently, the fluorescent intensities for a 1 bp mismatched dsDNA:PNA triplex (SEQ ID NO:2+Probe No. 2), a consecutive 2 bp mismatched triplex (SEQ ID NO:3+Probe No. 2), a consecutive 3 bp mismatched triplex (SEQ ID NO:4+Probe No.2) and a 3 bp deletion triplex (SEQ ID NO:5+Probe No.2) were 83%, 93%, 99% and 99.5% lower, respectively, than the perfectly matched dsDNA:PNA triplex (SEQ ID NO:1+Probe No. 2) at 30° C. As the temperature increased from 30° C. to 85° C., the degree of discrimination between perfect match and the base pair mismatches decreased. At 85° C., the 1 bp mismatch, 2 bp mismatch, 3 bp mismatch and 3 bp deletion hybrids yielded fluorescent intensities 65%, 76%, 94% and 95% lower, respectively, than that observed for the perfectly complementary sequences. Therefore, the hybridization assay of the invention is able to distinguish between wild-type sequences and those containing 1 bp, 2 bp or 3 bp mutations or deletions, without prior denaturation of sequences.

Example 5

Probe No. 3 was a 15-mer ssDNA probe identical in sequence and orientation to the 15-mer antiparallel PNA Probe No. 1 (SEQ ID NO:6). The probe had the following structure:

5'-CAC CAA AGA TGA TAT-3'

The specificity of the hybridization assay was further investigated by reacting ssDNA Probe No. 3 with the 50-mer wild-type and mutant dsDNA target sequences, in the absence of prior denaturation. The assay conditions were identical to those described in Example 4.

Enhanced by the DNA intercalator YOYO-1, dsDNA:ssDNA triplexes were formed between 30° C. and 65° C. Perfectly matched DNA triplexes, consisting of SEQ ID NO:1+Probe No. 3, yielded the highest fluorescent intensities (FIG. 5). In contrast, incompletely complementary probe and target combinations generating a 1 bp mismatch (SEQ ID NO:2+Probe No. 3), a consecutive 2 bp mismatch (SEQ ID NO:3+Probe No. 3), a consecutive 3 bp mismatch (SEQ ID NO:4+Probe No. 3) and a 3 bp deletion (SEQ ID NO:5+Probe No. 3) resulted in fluorescent intensities that were 57%, 94%, 97% and 98% lower at 30° C., and 47%, 79%, 92% and 91% lower at 65° C., respectively, than those observed with the perfectly matched sequences (FIG. 5). As the temperature increased above 65° C., the degree of discrimination between the perfect match and the base pair mismatches decreased, indicative of the gradual breakdown of the DNA triplex structure. By 85° C., the fluorescent intensities achieved by a 1 bp mismatch, a 2 bp mismatch, a 3 bp mismatch and a 3 bp deletion were 40%, 63%, 92% and 83% lower than that obtained by the perfect match (FIG. 5). The presence of YOYO-1 allowed a ssDNA probe to be used instead of a PNA probe to differentiate between perfectly complementary sequences and those containing 1 bp, 2 bp or 3 bp mismatches or deletions, without the requirement for prior denaturation.

Example 6

To ensure that the hybridization assay using ssDNA probes and dsDNA targets performed in the absence of prior denaturation would apply to probe and target DNAs possessing dramatically different percent GC contents (and consequently different melting temperatures), new 15-mer ssDNA probes and 50-mer dsDNA target sequences were synthesized, purified and annealed as above. Both ssDNA probes and dsDNA targets were dissolved in ddH$_2$O at a concentration of 1 pmole/$\mu$l.

SEQ ID NO:18 was a 50-mer dsDNA target sequence modified from SEQ ID NO:1, wherein the percent GC content was changed from 30% to 52%.

The sequence for the sense strand of the wild-type target DNA (SEQ ID NO:18) was: 5'-GAG CAC CAT GAC AGA CAC TGT CAT CTC TGG TGT GTC CTA CGA TGA CTC TG-3'.

The sequence for the antisense strand of the wild-type target DNA (SEQ ID NO:18) was: 5'-CAG AGT CAT CGT AGG ACA CAC CAG AGA TGA CAG TGT CTG TCA TGG TGC TC-3'.

SEQ ID NO:19 was a 50-mer mutant dsDNA target sequence identical to SEQ ID NO:18, except for a one base pair mutation (underlined), at which the sequence CAT was changed to CGT.

The sequence for the sense strand of mutant SEQ ID NO:19 was: 5'-GAG CAC CAT GAC AGA CAC TGT CGT CTC TGG TGT GTC CTA CGA TGA CTC TG-3'.

The sequence for the antisense strand of mutant SEQ ID NO:19 was: 5'-CAG AGT CAT CGT AGG ACA CAC CAG AGA CGA CAG TGT CTG TCA TGG TGC TC-3'.

SEQ ID NO:20 was a 50-mer mutant dsDNA target sequence identical to SEQ ID NO:18, except for a consecutive two base pair mutation (underlined), at which the sequence CAT was changed to ACT.

The sequence for the sense strand of mutant SEQ ID NO:20 was: 5'-GAG CAC CAT GAC AGA CAC TGT ACT CTC TGG TGT GTC CTA CGA TGA CTC TG-3'.

The sequence for the antisense strand of mutant SEQ ID NO:20 was: 5'-CAG AGT CAT CGT AGG ACA CAC CAG AGA GTA CAG TGT CTG TCA TGG TGC TC-3'.

SEQ ID NO:21 was a 50-mer dsDNA target sequence modified from SEQ ID NO:1, wherein the percent GC content was changed from 30% to 72%.

The sequence for the sense strand of the wild-type target DNA (SEQ ID NO:21) was: 5'-GAG CAC CCT CCC AGG CAC GGT CGT CCC TGG TGC GAC CTC CGA CGA GCG TG-3'.

The sequence for the antisense strand of the wild-type target DNA (SEQ ID NO:21) was: 5'-CAC GCT CGT CGG AGG TCG CAC CAG GGA CGA CCG TGC CTG GGA GGG TGC TC-3'

SEQ ID NO:22 was a 50-mer mutant dsDNA target sequence identical to SEQ ID NO:21, except for a one base pair mutation (underlined), at which the sequence CGT was changed to CAT.

The sequence for the sense strand of mutant SEQ ID NO:22 was: 5'-GAG CAC CCT CCC AGG CAC GGT CAT CCC TGG TGC GAC CTC CGA CGA GCG TG-3'.

The sequence for the antisense strand of mutant SEQ ID NO:22 was: 5'-CAC GCT CGT CGG AGG TCG CAC CAG GGA TGA CCG TGC CTG GGA GGG TGC TC-3'

SEQ ID NO:23 was a 50-mer mutant dsDNA target sequence identical to SEQ ID NO:21, except for a consecutive two base pair mutation (underlined), at which the sequence CGT was changed to ATT.

The sequence for the sense strand of mutant SEQ ID NO:23 was: 5'-GAG CAC CCT CCC AGG CAC GGT ATT CCC TGG TGC GAC CTC CGA CGA GCG TG-3'.

The sequence for the antisense strand of mutant SEQ ID NO:23 was: 5'-CAC GCT CGT CGG AGG TCG CAC CAG GGA ATA CCG TGC CTG GGA GGG TGC TC-3'.

Probe No. 4 was a 15-mer ssDNA probe designed to be completely complementary to a 15 nucleotide segment of the sense strand of the 50-mer wild-type target DNA (SEQ ID NO:18). The probe had the following structure (SEQ ID NO:24)

5'-CAC CAG AGA TGA CAG-3'.

Probe No. 5 was a 15-mer ssDNA probe designed to be completely complementary to a 15 nucleotide segment of the sense strand of the 50-mer wild-type target DNA (SEQ ID NO:21). The probe had the following structure (SEQ ID NO:25)

5'-CAC CAG GGA CGA CCG-3'.

The hybridization assay conditions were identical to those described in Example 4.

When the ssDNA Probe No. 4 (with a 53% GC content) was hybridized to the 50-mer wild-type dsDNA target (SEQ ID NO:18) and mutant dsDNA targets (SEQ ID NO:19 and SEQ ID NO:20), dsDNA:ssDNA triplexes were formed at low temperatures under non-denaturing conditions (FIG. 6A). While perfectly matched DNA triplexes achieved the highest fluorescent intensities, incompletely complementary triplexes with a 1 bp mismatch (SEQ ID NO:19+Probe No. 4) and a consecutive 2 bp mismatch (SEQ ID NO:20+Probe No. 4) produced fluorescent intensities that were 63% and 95% lower, respectively, than those observed with the perfectly matched sequences at 30° C. (FIG. 6A). As the temperature increased, the gradual breakdown of the DNA triplex structure occurred, resulting in diminished fluorescent intensities and less discrimination between perfect match and the base pair mismatches. By 85° C., very little difference in fluorescence was seen between perfectly matched sequences and those containing base pair mismatches (FIG. 6A).

Similarly, in the presence of YOYO-1, dsDNA:ssDNA triplexes were formed when the ssDNA Probe No. 5 (possessing a 73% GC content) was reacted with the corresponding 50-mer wild-type dsDNA target (SEQ ID NO:21) and mutant dsDNA targets (SEQ ID NO:22 and SEQ ID NO:23). The fluorescent intensities for a 1 bp mismatched DNA triplex (SEQ ID NO:22+Probe No. 5) and a consecutive 2 bp mismatched DNA triplex (SEQ ID NO:23+Probe No. 5) were 48% and 64% lower, respectively, than those obtained by the perfectly matched sequences at 30° C. (FIG. 6B). Fluorescence of all samples decreased as the temperature increased from 30° C. to 85° C., indicative of diminished YOYO-1 intercalation and DNA triplex breakdown.

Regardless of the percent GC content of the ssDNA probes and dsDNA targets, YOYO-1 was able to facilitate DNA triplex formation under non-denaturing conditions, to allow accurate discrimination between perfectly complementary sequences and those containing 1 or 2 bp mutations.

Example 7

The hybridization assays in Examples 5 and 6 proved the reliability of the invention to distinguish between wild-type DNA sequences and those containing base pair mismatches or deletions, without the requirement for prior denaturation, using ssDNA probes. These assays measured DNA triplex formation below the melting point of the dsDNA targets. Moreover, optimal discrimination between wild-type and mutated sequences was achieved at 30° C., the lowest temperature measured. To determine whether temperatures below 30° C. would be even more beneficial for the assay, the 15-mer ssDNA Probe No. 3 was reacted with the 50-mer wild-type dsDNA target (SEQ ID NO:1) or with the 50-mer mutant dsDNA target (SEQ ID NO:2) between 5° C. and 30° C.

In FIG. 7A, 2 pmoles of dsDNA target was reacted with 2 pmoles of ssDNA Probe No. 3 in a 40 μl reaction mixture containing 0.5×TBE and 500 nM of YOYO-1. In FIG. 7B, 500 fmoles (i.e., $10^{-15}$ moles) of dsDNA target was reacted with 500 fmoles of ssDNA Probe No. 3 in a 40 μl reaction mixture containing 0.5×TBE and 250 nM of YOYO-1. The reaction mixtures were incubated at room temperature (21° C.) for 5 minutes, transferred to a quartz cuvette, and then irradiated with an argon ion laser beam at 30° C. as performed in Examples 4 to 6. The cuvettes containing the samples were subsequently placed on ice. When the temperature of each sample reached 2° C. (as determined by the temperature probe placed directly into each sample), the samples were transferred to the measurement chamber and monitored repeatedly for fluorescent emission as the temperature increased with time from 5° C. to 30° C. Maximum fluorescent intensities were plotted as a function of temperature for each sample analyzed.

Optimal discrimination between the perfectly complementary DNA triplexes (SEQ ID NO:1+Probe No. 3) and the DNA triplexes containing a 1 bp mismatch (SEQ ID NO:2+Probe No. 3) was observed at 5° C. for both concentrations of DNA tested (FIGS. 7A and 7B). However, the difference in fluorescent intensities between completely and incompletely complementary DNA triplexes did not vary dramatically as the temperature increased from 5° C. to 30° C. At a concentration of 1 pmole/20 μl of both probe and target, the 1 bp mismatched DNA triplexes produced fluorescent intensities that were 84% and 77% lower at 5° C. and 30° C., respectively, than those obtained with the perfectly matched sequences (FIG. 7A). Similarly, at a four-fold lower concentration of probe and target, a difference of 63% and 50% in fluorescent intensities was observed at 5° C. and 30° C., respectively, between the perfectly matched and mismatched DNA triplexes (FIG. 7B). The fluorescent intensities of all samples measured at 30° C. before and after cooling to 5° C. were very similar (data not shown). Although maximal differences were observed at 5° C., for convenience, the non-denaturing hybridization assay may be reliably performed at room temperature.

Example 8

The sensitivity of the hybridization assay was tested by reacting decreasing concentrations of parallel PNA Probe No. 2 or ssDNA Probe No. 3 with decreasing concentrations of 50-mer wild-type or mutant dsDNA targets (SEQ ID NO:1 and SEQ ID NO:2, respectively), under non-denaturing conditions between 27° C. and 32° C. (FIG. 8).

The hybridization reaction mixture (40 μl) contained the following: 20 fmoles to 2 pmoles of target dsDNA, 20 fmoles to 2 pmoles of ssDNA Probe No. 3 or parallel PNA Probe No. 2, 0.5×TBE and 2.5 nM to 500 nM of YOYO-1. In every sample, the target sequences and probe sequences were maintained at identical concentrations. The assay conditions were identical to those described in Example 4.

When 1 pmole/20 μl of parallel PNA Probe No. 2 or ssDNA Probe No. 3 was hybridized to 1 pmole/20 μl of dsDNA target sequences at the normal YOYO-1 concentration of 500 nM, the dsDNA:PNA and dsDNA:ssDNA triplexes resulting from a 1 bp mismatch produced fluorescent intensities ranging from 93% to 94% and 56% to 54% lower, respectively, than those observed from the perfectly matched triplexes at 27° C. to 32° C. (data not shown).

At a concentration of 10 fmole/20 µl of both probe and target (i.e. a 100-fold lower concentration), the 1 bp mismatched dsDNA:PNA hybrid achieved fluorescent intensities ranging from 85% to 83% lower than that obtained from the perfectly complementary triplexes at 27° C. to 32° C. when 25 nM YOYO-1 was used (FIG. 8A). Similarly, when 10 fmole/20 µl of ssDNA Probe No. 3 was reacted with 10 fmole/20 µl of the dsDNA target sequences, in the presence of 10 nM YOYO-1, the fluorescent intensities generated by a 1 bp mismatch were 90% to 84% lower than that produced by perfectly matched DNA triplexes at 27° C. to 32° C. (FIG. 8B), proving the extreme sensitivity of the hybridization assay, even at very low concentrations of probe and target.

A wide range of YOYO-1 concentrations was tolerated at each concentration of probe and target tested. When 10 fmoles/20 µl of both probe and target were hybridized, the optimal concentrations of YOYO-1 were 25 nM to 2.5 nM (for a parallel PNA probe) and 10 nM to 2.5 nM (for a ssDNA probe), yielding differences of fluorescent intensities ranging from 90% to 71% between perfectly matched and mismatched sequences (data not shown). Collectively, these results confirmed the extreme sensitivity and reliability of the non-denaturing hybridization assay to distinguish between wild-type sequences and those containing various base pair mutations.

While the invention has been described in detail and with reference to specific examples thereof, it will be apparent to one skilled in the art that various changes and modifications can be made therein without departing from the spirit and scope thereof.

What is claimed is:

1. A method for assaying binding, said method comprising:

providing a target comprising at least one nucleic acid sequence;

providing a probe comprising a nucleic acid or nucleic acid analog sequence incompletely complementary to at least a portion of said target;

providing an intercalating agent, wherein either said probe or said intercalating agent comprises a fluorophore;

adding said probe, said target and said intercalating agent to a hybridization medium to provide a test sample comprising triplexes of said probe and said target, wherein said triplexes comprise base triplets, and all said base triplets of said triplexes are members selected from the group consisting of A-T-A, T-A-T, U-A-T, T-A-U, A-U-A, U-A-U, G-C-G and C-G-C, and wherein at least one of said base triplets is T-A-T, U-A-T, T-A-U, U-A-U or C-G-C, and at least one other of said base triplets is A-T-A, G-C-G or A-U-A;

irradiating said test sample with exciting radiation to cause said fluorophore to emit fluorescent radiation;

detecting an intensity of said fluorescent radiation, wherein said intensity increases with increasing binding affinity between said probe and said target; and determining from said intensity a number of mismatched bases, an identity of a mismatched base and/or a location of a mismatch between said probe and said target to assay binding, wherein said determining is accomplished by calibrating said intensity against intensities exhibited by reference probes combined with said target and said intercalating agent, said reference probes differing from each other by at least one base, wherein said method is conducted without denaturing said target or said probe.

2. The method of claim 1, wherein relative to said target, each of said probe and said reference probes is a different member selected from the group consisting of a perfect match, a one-base mismatch, a two-base mismatch, a three-base mismatch, a one-base deletion, a two-base deletion and a three-base deletion, provided that said probe cannot be said perfect match.

3. The method of claim 1, further comprising quantifying said binding affinity by determining a numeric value of said binding affinity as a function of said intensity.

4. A The method of claim 1, wherein said method is a homogeneous assay conducted without providing a signal quenching agent on said target or on said probe.

5. The method of claim 1, wherein said method is a homogeneous assay conducted without prior denaturation of said target.

6. The method of claim 1, wherein said method is a homogeneous assay conducted without PCR amplification of said target.

7. The method of claim 1, wherein said target is dsDNA and said probe hybridizes specifically with said target to form a triplex.

8. The method of claim 7, wherein said probe is ssDNA or RNA.

9. The method of claim 1, wherein said probe has a partially charged backbone.

10. The method of claim 1, wherein said probe has an uncharged backbone.

11. The method of claim 10, wherein said probe comprises a PNA sequence.

12. The method of claim 1, wherein said probe is ssPNA prepared by parallel synthesis.

13. The method of claim 12, wherein said probe and said target are the same length.

14. The method of claim 1, wherein said probe is 6 to 30 nucleotides long.

15. The method of claim 1, wherein said probe is 15 nucleotides long.

16. The method of claim 1, wherein said intercalating agent is covalently bound to said probe.

17. The method of claim 1, wherein said intercalating agent is not covalently bound to said probe or said target when added to said hybridization medium.

18. The method of claim 1, wherein said intercalating agent is a member selected from the group consisting of YOYO-1, TOTO-1, ethidium bromide, ethidium homodimer-1, ethidium homodimer-2 and acridine.

19. The method of claim 1, wherein said probe consists essentially of said nucleic acid or said nucleic acid analog sequence.

20. The method of claim 1, wherein said exciting radiation is emitted from an argon ion laser at a wavelength from about 200 nm to about 1000 nm.

21. The method of claim 1, entirely conducted at temperatures within a range of 5 to 85° C.

22. The method of claim 1, conducted at temperatures below 25° C.

23. The method of claim 1, wherein a reliability of said method is independent of probe or target base sequence and independent of probe or target guanine and cytosine content.

24. The method of claim 1, wherein said test sample has a volume of about 20 microliters containing about 10 femtomoles of target and about 10 femtomoles of probe.

25. The method of claim 1, wherein a concentration of said target in said sample is not more than $5 \times 10^{-10}$ M.

26. The method of claim 25, wherein a concentration of said probe in said sample is not more than $5 \times 10^{-10}$ M.

27. The method of claim 1, wherein said intercalating agent comprises a fluorophore and wherein a wavelength at which said intercalating agent fluoresces shifts to a second wavelength upon intercalation, a difference between said wavelength and said second wavelength indicating whether a complex between said probe and said target is a duplex or a triplex and whether said target is DNA or RNA.

28. The method of claim 1, conducted in a solution within a well or on an impermeable surface.

29. The method of claim 1, conducted on a biochip.

30. A method for assaying binding, said method comprising:

providing a target comprising at least one nucleic acid sequence;

providing a probe comprising a first fluorophore and a nucleic acid or nucleic acid analog sequence incompletely complementary to at least a portion of said target;

providing an intercalating agent comprising a second fluorophore, wherein said second fluorophore and said first fluorophore fluoresce at different wavelengths;

adding said probe, said target and said intercalating agent to a hybridization medium to provide a test sample comprising triplexes of said probe and said target, wherein said triplexes comprise base triplets, and all said base triplets of said triplexes are members selected from the group consisting of A-T-A, T-A-T, U-A-T, T-A-U, A-U-A, U-A-U, G-C-G and C-G-C, and wherein at least one of said base triplets is T-A-T, U-A-T, T-A-U, U-A-U or C-G-C, and at least one other of said base triplets is A-T-A, G-C-G or A-U-A;

irradiating said test sample with exciting radiation to cause at least one of said first fluorophore and said second fluorophore to emit fluorescent radiation;

detecting an intensity of said fluorescent radiation, wherein said intensity increases with increasing binding affinity between said probe and said target; and determining from said intensity a number of mismatched bases, an identity of a mismatched base and/or a location of a mismatch between said probe and said target to assay binding, wherein said determining is accomplished by calibrating said intensity against intensities exhibited by reference probes combined with said target and said intercalating agent, said reference probes differing from each other by at least one base, wherein said method is conducted without denaturing said target or said probe.

31. A method for assaying binding, said method comprising:

providing a target comprising at least one nucleic acid sequence;

providing a probe comprising a nucleic acid or nucleic acid analog sequence;

providing an intercalating agent, wherein either said probe or said intercalating agent comprises a fluorophore;

adding said probe, said target and said intercalating agent to a hybridization medium to provide a test sample comprising triplexes of said probe and said target, wherein said triplexes comprise base triplets, and all said base triplets of said triplexes are members selected from the group consisting of A-T-A, T-A-T, U-A-T, T-A-U, ARU-A, U-A-U, G-C-G and C-G-C, and wherein at least one of said base triplets is T-A-T, U-A-T, T-A-U, U-A-U or C-G-C, and at least one other of said base triplets is A-T-A, G-C-G or A-U-A;

irradiating said test sample with exciting radiation to cause said fluorophore to emit fluorescent radiation;

detecting an intensity of said fluorescent radiation, wherein said intensity increases with increasing binding affinity between said probe and said target;

calibrating said intensity against intensities exhibited by reference probes combined with said target and said intercalating agent, wherein relative to said target, each of said probe and said reference probes is a different member selected from the group consisting of a perfect match, a one-base mismatch, a two-base mismatch, a three-base mismatch, a one-base deletion, a two-base deletion and a three-base deletion; and determining from said calibrating a number of mismatched bases, an identity of a mismatched base and/or a location of a mismatch between said probe and said target to assay binding, wherein said method is conducted without denaturing said target or said probe.

* * * * *